(12) United States Patent
Kenyon et al.

(10) Patent No.: US 10,871,165 B2
(45) Date of Patent: Dec. 22, 2020

(54) SINGLE OR MULTIPLE STAGE BLOWER AND NESTED VOLUTE(S) AND/OR IMPELLER(S) THEREFOR

(71) Applicant: ResMed Motor Technologies Inc., Chatsworth, CA (US)

(72) Inventors: Barton John Kenyon, Sydney (AU); Nicholas Jerome Reed, Sydney (AU); Andrew Wilson, Sydney (AU); Ian Malcolm Smith, Sydney (AU)

(73) Assignee: ResMed Motor Technologies Inc., Chatsworth, CA (US)

( * ) Notice: Subject to any disclaimer, the term of this patent is extended or adjusted under 35 U.S.C. 154(b) by 72 days.

(21) Appl. No.: 16/377,456

(22) Filed: Apr. 8, 2019

(65) Prior Publication Data

US 2019/0234410 A1 Aug. 1, 2019

Related U.S. Application Data

(63) Continuation of application No. 15/334,467, filed on Oct. 26, 2016, now Pat. No. 10,267,320, which is a (Continued)

(51) Int. Cl.
*F04D 17/16* (2006.01)
*A61M 16/00* (2006.01)
(Continued)

(52) U.S. Cl.
CPC ....... *F04D 17/164* (2013.01); *A61M 16/0057* (2013.01); *A61M 16/0066* (2013.01);
(Continued)

(58) Field of Classification Search
CPC .......... A61M 16/0066; A61M 16/0069; A61M 16/0057; F04D 17/164; F04D 25/0606;
(Continued)

(56) References Cited

U.S. PATENT DOCUMENTS 3,594,102 A 7/1971 Oden
3,874,023 A 4/1975 Tschudy
(Continued)

FOREIGN PATENT DOCUMENTS

CN 1159531 7/2004
EP 0295455 9/1992
(Continued)

OTHER PUBLICATIONS

Extended European Search Report issued in corresponding European Patent Application No. 16 15 3742.8 dated Jun. 14, 2016.
(Continued)

*Primary Examiner* — Igor Kershteyn
(74) *Attorney, Agent, or Firm* — Nixon & Vanderhye P.C.

(57) ABSTRACT

A double-ended blower includes a blower motor assembly supporting opposed first and second shaft ends. The first and second shaft ends have respective first and second impellers attached thereto and enclosed within first and second volutes, respectively. The first volute is connected to an inlet and the second volute is connected to an outlet. The blower motor assembly is supported in a chassis enclosure and a radially outer inter-stage path is between the first and second volute. The second volute is at least partially substantially concentrically nested with the radially outer inter-stage gas path.

20 Claims, 31 Drawing Sheets

Related U.S. Application Data continuation of application No. 14/095,285, filed on Dec. 3, 2013, now Pat. No. 9,512,729, which is a continuation of application No. 13/532,227, filed on Jun. 25, 2012, now Pat. No. 8,628,302, which is a continuation of application No. 12/083,350, filed as application No. PCT/AU2006/001617 on Oct. 27, 2006, now Pat. No. 8,272,837.

(60) Provisional application No. 60/730,875, filed on Oct. 28, 2005, provisional application No. 60/841,202, filed on Aug. 31, 2006, provisional application No. 60/775,333, filed on Feb. 22, 2006.

(51) Int. Cl.
| | |
|---|---|
| *F01D 5/22* | (2006.01) |
| *F04D 25/06* | (2006.01) |
| *F04D 29/02* | (2006.01) |
| *F04D 29/08* | (2006.01) |
| *F04D 29/30* | (2006.01) |
| *F04D 29/42* | (2006.01) |
| *F04D 29/44* | (2006.01) |
| *F04D 29/60* | (2006.01) |
| *F04D 29/66* | (2006.01) |

(52) U.S. Cl.
CPC ......... *A61M 16/0069* (2014.02); *F01D 5/225* (2013.01); *F04D 25/0606* (2013.01); *F04D 29/023* (2013.01); *F04D 29/083* (2013.01); *F04D 29/30* (2013.01); *F04D 29/4226* (2013.01); *F04D 29/444* (2013.01); *F04D 29/601* (2013.01); *F04D 29/668* (2013.01)

(58) Field of Classification Search
CPC .. F04D 29/4226; F04D 29/023; F04D 29/601; F04D 29/668; F04D 29/083; F04D 29/30; F04D 29/444; F01D 5/225
See application file for complete search history.

(56) References Cited

U.S. PATENT DOCUMENTS

| | | | |
|---|---|---|---|
| 4,355,792 A | 10/1982 | Fukuda et al. | |
| 4,647,271 A | 3/1987 | Nagai et al. | |
| 4,767,285 A | 8/1988 | Jyoraku et al. | |
| 4,927,119 A | 5/1990 | Frost | |
| 5,127,622 A | 7/1992 | Whelpley et al. | |
| 5,364,086 A | 11/1994 | Paton | |
| 5,704,345 A | 1/1998 | Berthon-Jones et al. | |
| 5,813,831 A | 9/1998 | Matsunaga et al. | |
| 5,893,705 A | 4/1999 | Khan et al. | |
| 5,964,576 A | 10/1999 | Fujita et al. | |
| 6,299,409 B1 | 10/2001 | Matsunaga et al. | |
| 6,315,526 B1 | 11/2001 | Jones | |
| 6,394,432 B1 | 5/2002 | Whiteford | |
| 6,558,120 B2 | 5/2003 | Kim et al. | |
| 6,565,334 B1 | 5/2003 | Bradbury et al. | |
| 6,685,430 B2 | 2/2004 | Chapman | |
| 6,695,584 B2 | 2/2004 | Kim et al. | |
| 6,755,615 B2 | 6/2004 | Chapman | |
| 6,910,483 B2 | 6/2005 | Daly et al. | |
| 6,971,846 B2 | 12/2005 | Ochiai et al. | |
| 7,179,053 B2 | 2/2007 | Kim et al. | |
| 7,281,898 B2 | 10/2007 | Baek et al. | |
| D642,676 S | 8/2011 | Kenyon | |
| 8,272,837 B2 | 9/2012 | Kenyon et al. | |
| 8,628,302 B2 | 1/2014 | Kenyon et al. | |
| 9,022,731 B2 * | 5/2015 | Seccareccia | F04D 29/584 415/206 |
| 9,127,692 B2 * | 9/2015 | Goenka | F04D 29/441 |
| 9,194,398 B2 * | 11/2015 | Fujimoto | F04D 29/4246 |
| 2001/0014290 A1 | 8/2001 | Takura et al. | |
| 2003/0168064 A1 | 9/2003 | Daly et al. | |
| 2004/0247441 A1 | 12/2004 | Kim et al. | |
| 2005/0152781 A1 | 7/2005 | Back et al. | |
| 2005/0163614 A1 | 7/2005 | Chapman | |
| 2005/0169750 A1 | 8/2005 | Kim et al. | |
| 2009/0196759 A1 | 8/2009 | Eschborn et al. | |
| 2014/0119921 A1 | 5/2014 | Kenyon et al. | |
| 2017/0045056 A1 | 2/2017 | Kenyon et al. | |

FOREIGN PATENT DOCUMENTS

| | | |
|---|---|---|
| EP | 0 627 560 | 12/1994 |
| EP | 1 184 575 A2 | 3/2002 |
| EP | 1 571 344 | 9/2005 |
| JP | H 08-109897 | 4/1996 |
| JP | H09-079199 | 3/1997 |
| JP | 3055238 | 4/2000 |
| JP | 2002-532207 | 10/2002 |
| JP | 2003-314492 | 11/2003 |
| JP | 2004-515677 | 5/2004 |
| JP | 2005-171962 | 6/2005 |
| JP | 2005-248950 | 9/2005 |
| JP | 2006-257912 | 9/2006 |
| JP | 2007-531540 | 11/2008 |
| KR | 2002-0019159 | 3/2002 |
| WO | 1999/000601 | 1/1999 |
| WO | 00/37135 | 6/2000 |
| WO | 2000/038771 | 7/2000 |
| WO | 02/45862 | 6/2002 |
| WO | 2004/079201 | 9/2004 |
| WO | 2004/108198 | 12/2004 |
| WO | 2004/112873 | 12/2004 |
| WO | 2005/009501 | 2/2005 |

OTHER PUBLICATIONS

Fourth Office Action issued in corresponding Chinese Patent Application No. 201310054938.7 dated Jul. 6, 2016, with English language translation thereof.
Notice of Allowance issued in corresponding Japanese Appl. No. 2012-079424 dated May 7, 2014, with English translation thereof.
Office Action issued in corresponding Japanese Appln. No. 2012-097424 dated Sep. 3, 2013, with English translation thereof.
Patent Examination Report No. 2 issued in corresponding Australian Appln. No. 2013202608 dated Apr. 21, 2015.
Notice of Acceptance issued in corresponding Australian Appln. No. 2013202608 dated May 5, 2015.
Second Office Action issued in corresponding Chinese Application No. 201310054938.7 dated Jun. 30, 2015, with English translation thereof.
Office Action issued in corresponding Chinese Appl. No. 201310054938.7 dated Dec. 3, 2014 with English language translation thereof.
U.S. Appl. No. 10/864,869 (2005/0103339), filed Jun. 2004 (May 2005), Daly.
U.S. Appl. No. 10/533,840 (2006/0033681), filed May 2005 (Feb. 2006), Hashimoto et al.
Examination Report issued in corresponding EP Application No. 06 804 445.2 dated Aug. 28, 2014.
Office Action issued in related Chinese Appln. No. 200680040333.0 (dated Dec. 27, 2010) w/English translation.
U.S. Appl. No. 12/083,937, filed Apr. 22, 2008.
U.S. Appl. No. 11/480,568, filed Jul. 5, 2006.
International Search Report for PCT/AU2006/001616, dated Dec. 21, 2006.
Chinese Official Action, "Notification of Second Office Action" dated Apr. 5, 2012 (with English translation) (14 pages) for corresponding Chinese Application No. 200680040333.0 filed Oct. 27, 2006.
Examiner's Report issued in related AU Appln. No. 2006308435 (dated Jan. 25, 2012).
Examination Report issued in related New Zealand Appln. No. 590498 (dated Jan. 18, 2011).

(56) References Cited

OTHER PUBLICATIONS

International Search Report for PCT/AU2006/001617, dated Dec. 21, 2006.
Office Action issued in related JP Appln. No. 2008-536884 (dated Dec. 6, 2011).
Australian Patent Examination Report No. 1 issued in Australian Appln. No. 2013202608 dated May 5, 2014.
Third Office Action issued in corresponding Chinese Application No. 201310054938.7 dated Jan. 5, 2016 with English translation thereof.
Japanese Office Action issued in corresponding Appln. No. 2013-249893 dated Dec. 1, 2014 with English language translation thereof.
Communication dated Sep. 13, 2017 issued in European Application No. 16 153 742.8 (5 pages).

* cited by examiner

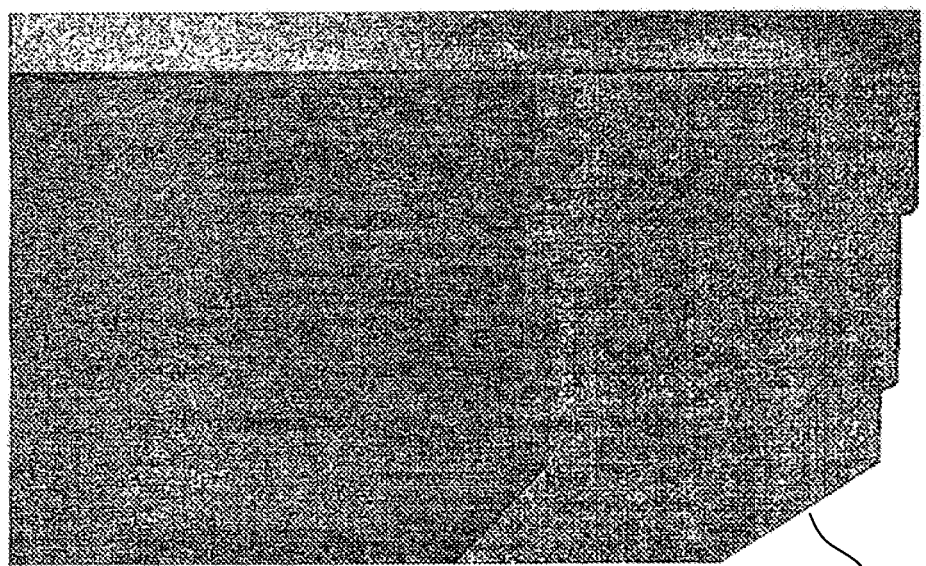
88.3  FIG. 10-7  99.1
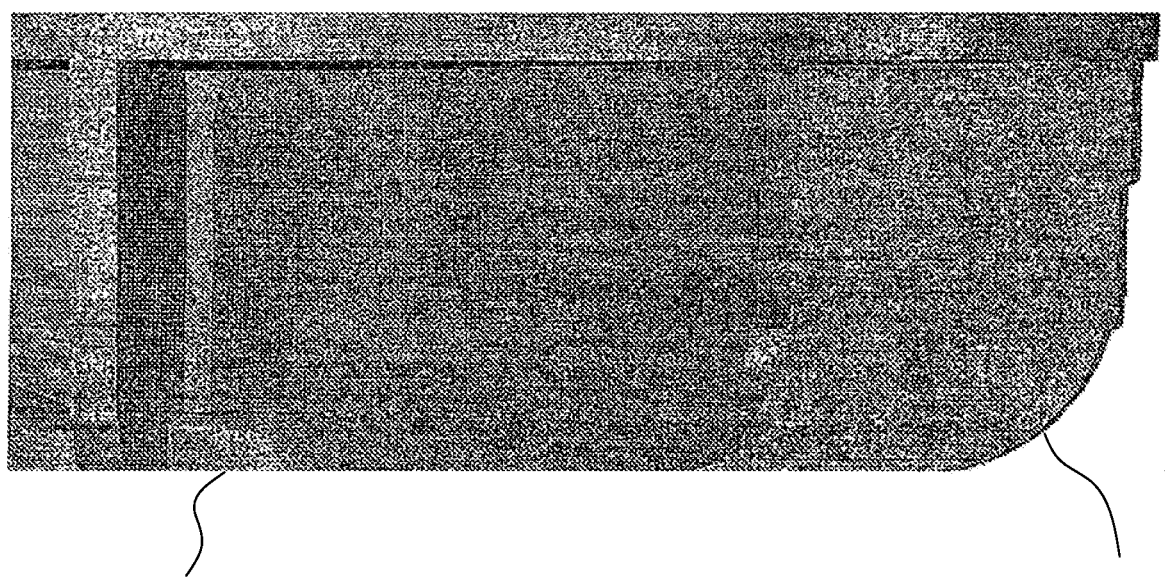
88.3  FIG. 10-8  99.2

SINGLE OR MULTIPLE STAGE BLOWER AND NESTED VOLUTE(S) AND/OR IMPELLER(S) THEREFOR

CROSS REFERENCE TO PRIORITY APPLICATIONS

This application is a continuation of U.S. patent application Ser. No. 15/334,467, filed Oct. 26, 2016, now allowed, which is a continuation of Ser. No. 14/095,285, filed Dec. 3, 2013, now U.S. Pat. No. 9,512,729, which is a continuation of U.S. patent application Ser. No. 13/532,227, filed Jun. 25, 2012, now U.S. Pat. No. 8,628,302, which is a continuation of U.S. patent application Ser. No. 12/083,350, filed Dec. 1, 2008, now U.S. Pat. No. 8,272,837, which is a U.S. National Phase of International Application No. PCT/AU2006/001617, filed Oct. 27, 2006, which designated the U.S. and claims the benefit of U.S. Provisional Application No. 60/730,875, filed Oct. 28, 2005, U.S. Provisional Application No. 60/841,202, filed Aug. 31, 2006, and U.S. Provisional Application No. 60/775,333, filed Feb. 22, 2006, each of which is incorporated herein by reference in its entirety.

BACKGROUND OF THE INVENTION

1. Field of the Invention

The present invention relates to an apparatus for supplying breathable gas to a human, used in, for example, Continuous Positive Airway Pressure (CPAP) treatment of Obstructive Sleep Apnea (OSA), other respiratory diseases and disorders such as emphysema, or the application of assisted ventilation.

2. Description of Related Art

CPAP treatment of OSA, a form of Noninvasive Positive Pressure Ventilation (NIPPV), involves the delivery of a pressurized breathable gas, usually air, to a patient's airways using a conduit and mask. Gas pressures employed for CPAP can range, e.g., from 4 cm $H_2O$ to 30 cm $H_2O$ (typically in the range of 8-15 $cmH_2O$), at flow rates of up to 180 L/min (measured at the mask), depending on patient requirements. The pressurized gas acts as a pneumatic splint for the patient's airway, preventing airway collapse, especially during the inspiratory phase of respiration.

Typically, the pressure at which a patient is ventilated during CPAP is varied according to the phase of the patient's breathing cycle. For example, the ventilation apparatus may be pre-set, e.g., using control algorithms, to deliver two pressures, an inspiratory positive airway pressure (IPAP (e.g., 4-8 $cmH_2O$)) during the inspiration phase of the respiratory cycle, and an expiratory positive airway pressure (EPAP (e.g., 10-20 $cmH_2O$)) during the expiration phase of the respiratory cycle. An ideal system for CPAP is able to switch between IPAP and EPAP pressures quickly, efficiently, and quietly, while providing maximum pressure support to the patient during the early part of the inspiratory phase.

In a traditional CPAP system, the air supply to the patient is pressurized by a blower having a single impeller, i.e., a single stage blower. The impeller is enclosed in a volute, or housing, in which the entering gas is trapped while pressurized by the spinning impeller. The pressurized gas gradually leaves the volute and travels to the patient's mask, e.g., via an air delivery path typically including an air delivery tube.

Other blowers utilize a pair of impellers with, for example, one on either side of the motor but fixed to a common output shaft. Such configurations are disclosed in commonly-owned U.S. Pat. No. 6,910,483 and in commonly-owned co-pending application Ser. No. 10/864,869, filed Jun. 10, 2004, each incorporated herein by reference in its entirety.

Single-stage blowers are often noisy and are not as responsive as two-stage blowers in that they require longer periods of time to achieve the desired pressure. Two-stage blowers tend to generate less noise since they can run at lower speeds to generate the desired pressure, and are more responsive. On the other hand, two stage or double-ended blowers tend to be too large for certain applications.

SUMMARY OF THE INVENTION

One aspect of the present invention relates generally to a single or multiple stage, e.g., two or more stages, variable-speed blower assembly that provides faster pressure response time with increased reliability and less acoustic noise, and in a smaller package.

Another aspect of the present invention relates to an impeller for use with an blower assembly for the treatment of sleep disordered breathing.

To this end, the exemplary embodiments described herein have various structural aspects that are particularly advantageous. One aspect relates to the blower motor assembly, and specifically, to the elimination of a typical motor housing, thus reducing both size and weight. With the elimination of the motor housing, the space between the motor body and the chassis in which the motor body is supported, defines the first volute for pressurized air between the first and second stage impellers.

In an embodiment, an annular dividing seal between the motor body and chassis divides the substantially radial space into two portions. A first or upper portion houses the upper half of the blower motor assembly and includes a gas inlet for supplying unpressurized gas to a first stage impeller located at the upper end of the motor. The second or lower portion houses the lower half of the blower motor assembly and includes the first volute and a second gas inlet to a second stage impeller located at the lower or opposite end of the motor. In other words, a first volute in the upper portion supplies gas to the second inlet at the second stage impeller by means of an inter-stage path, and a second volute located within the motor body, and axially beneath the first volute, moves the air to the chassis outlet. This axially nested arrangement of the volutes and the inter-stage path provides significant space savings.

Another structural aspect of an exemplary embodiment relates to the support of the blower motor assembly on a plurality of springs within the chassis, providing vibrational isolation of the blower motor assembly from the chassis. Another related feature is the utilization of a plastic material for the blower motor assembly top cover; a relatively soft, flexible polymer, such as silicone rubber, for both the dividing seal between the blower motor assembly and chassis and for the coupling between the blower motor assembly outlet and the chassis outlet; and metals such as aluminum or magnesium for the motor cap and motor body. The combination of dissimilar materials for various component parts tends to damp out vibration and thus reduce noise.

In order to reduce inertia and thus enhance responsiveness in terms of pressure variations, the first and second stage impellers are of the double-shroud type, but the pair of shrouds on the respective impellers are not identical. Rather, one shroud extends from a center hub of the impeller a relatively short distance in a radially outward direction. The other shroud extends radially outwardly to the outer edges of the impeller blades, but with a center opening having an inner diameter similar to the outer diameter of the smaller shroud. This configuration, sometimes referred to herein as an "alternating shroud" configuration, facilitates manufacture and reduces inertia by reducing the amount of material in the outer portion of the impeller, without sacrificing impeller rigidity requirements. This approach also reduces the sensitivity to variations in the gap between impeller and cover.

In another embodiment, nested volutes components are fastened together about the blower motor, and are at the same time sandwiched between upper and lower lids or covers that may be snap-fit onto (or otherwise suitably attached to) the respective volutes components, providing an axially compact and easily assembled unit. This assembly is also adapted to be received in a cup-shaped, open-ended flexible sleeve.

The impeller vanes or blades are continuously curved in a radial direction, but also taper in width in the radially outer portions, along edges adjacent the smaller-diameter shroud. Moreover, the outermost transverse edges of the blades or vanes may be stepped along their respective transverse widths. This design reduces turbulence noise at the tips of the blades and in addition, the impellers are preferably made of a polypropylene rather than the conventional polycarbonate so as to provide even further acoustic damping properties.

In an alternative embodiment, the larger diameter shroud may have a truncated frusto-conical shape, with a corresponding taper along one edge of the impeller blades in a radial length direction, such that at least the radially outer portions of the blades taper in width in a radially outer direction.

Another feature relates to having a matching taper along an adjacent surface of the one or both of the top and bottom lids or covers to provide a substantially constant distance between the tapered blade edges and adjacent lid or cover surfaces.

Preferably, the first and second stage impellers are secured at opposite ends of the motor output shaft for rotation about a common axis. The impellers are placed in fluid communication with one another by the gas flow path such that they cooperatively pressurize gas in the first and second volutes before exiting the chassis outlet.

Accordingly, in one aspect, the invention relates to a double-ended blower comprising a blower motor assembly supporting opposed first and second shaft ends, the first and second shaft ends having respective first and second impellers attached thereto and enclosed within first and second volutes, respectively, wherein the first volute is connected to an inlet and the second volute is connected to an outlet; and the blower motor assembly supported in a chassis enclosure; a radially outer inter-stage path between the first and second volute, wherein the second volute is at least partially substantially concentrically nested with the radially outer inter-stage gas path.

In another aspect, the invention relates to a double-ended blower comprising a blower motor assembly supporting opposed first and second shaft ends, the first and second shaft ends having respective first and second impellers attached thereto; the blower motor assembly supported within a chassis enclosure and comprising a motor body including a bottom wall, a peripheral sidewall and a top cover and wherein the top cover is provided with a flexible seal that engages an inner wall of the chassis enclosure.

In another aspect, the invention relates to a blower comprising a blower motor assembly supporting a shaft with a shaft end provided with an impeller, said impeller having a plurality of curved vanes, each vane tapering in width in radially outer portions thereof.

Another aspect of the invention is directed to an impeller comprising a top shroud; a bottom shroud; and a plurality of vanes extending from the top shroud to the bottom shroud, each said vane including a top edge at a radially inner portion of the vane in contact with the top shroud and a bottom edge at a radially outer portion of the vane in contact with the bottom shroud, such that a radially inner portion of the vane at the bottom edge of each vane is not in contact with or adjacent the bottom shroud and a radially outer portion of the vane at the top edge of each vane is not in contact with or adjacent the top shroud.

In still another aspect, the invention relates to a double-ended blower comprising: a blower motor including oppositely extending first and second shaft ends, supporting first stage and second stage impellers, respectively; first and second volute components on opposite sides of the motor and secured to each other; an upper lid or cover attached to the first volute and a lower lid or cover attached to the second volute, the first volute component and the upper lid or cover defining a first volute in which the first stage impeller is mounted, the second volute component and the lower lid or cover defining a second volute in which the second impeller is mounted, the first and second volutes connected by a spiral inter-stage gas path substantially concentric with the first and second shaft ends.

These and other aspects will be described in or apparent from the following detailed description of preferred embodiments.

BRIEF DESCRIPTION OF THE DRAWINGS

FIGS. 10-1 to 10-6 are views of an impeller according to another embodiment of the present invention;

FIGS. 10-7 to 10-10 are views of the impeller with three alternative embodiments of the chamfering of the vane or blade tips;

DETAILED DESCRIPTION OF ILLUSTRATED EMBODIMENTS a) General

Figure 1:
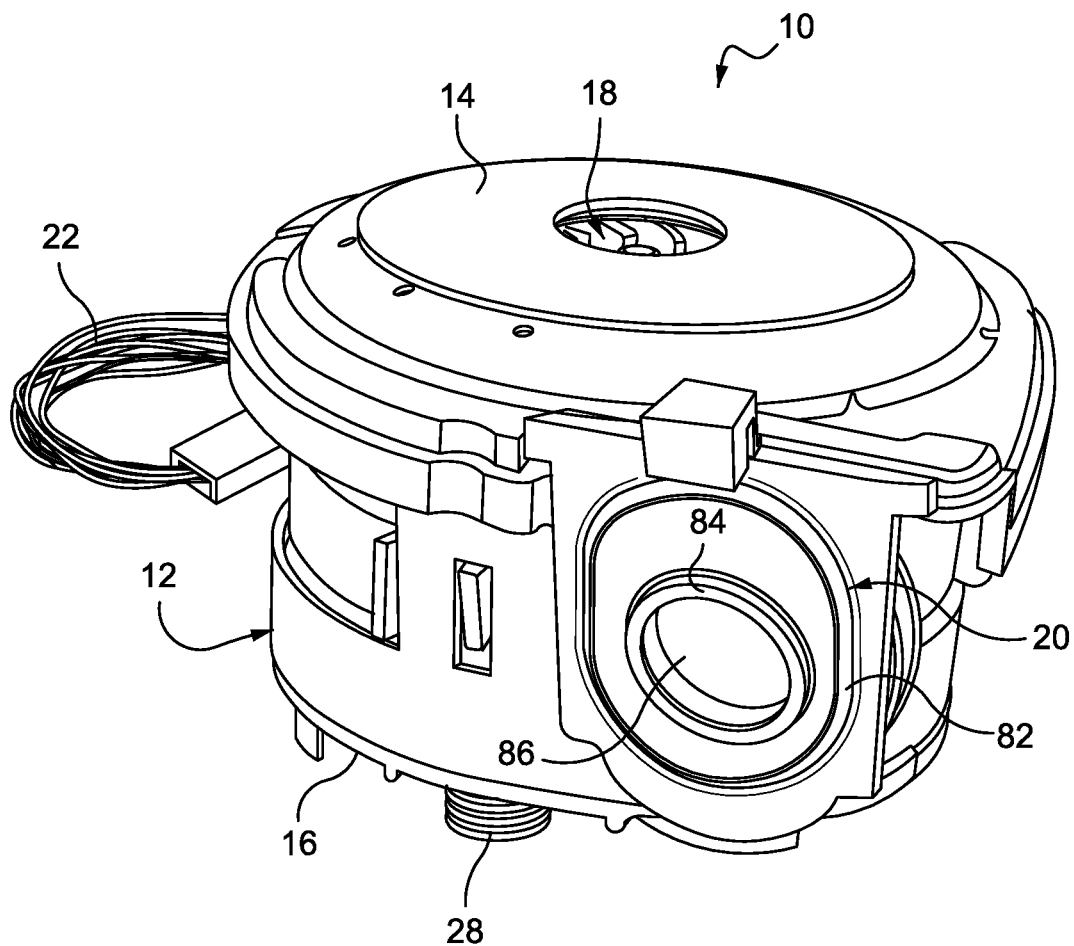
FIG. 1 is a perspective view of a blower motor assembly in accordance with the first exemplary embodiment of the invention.
Figure 2:
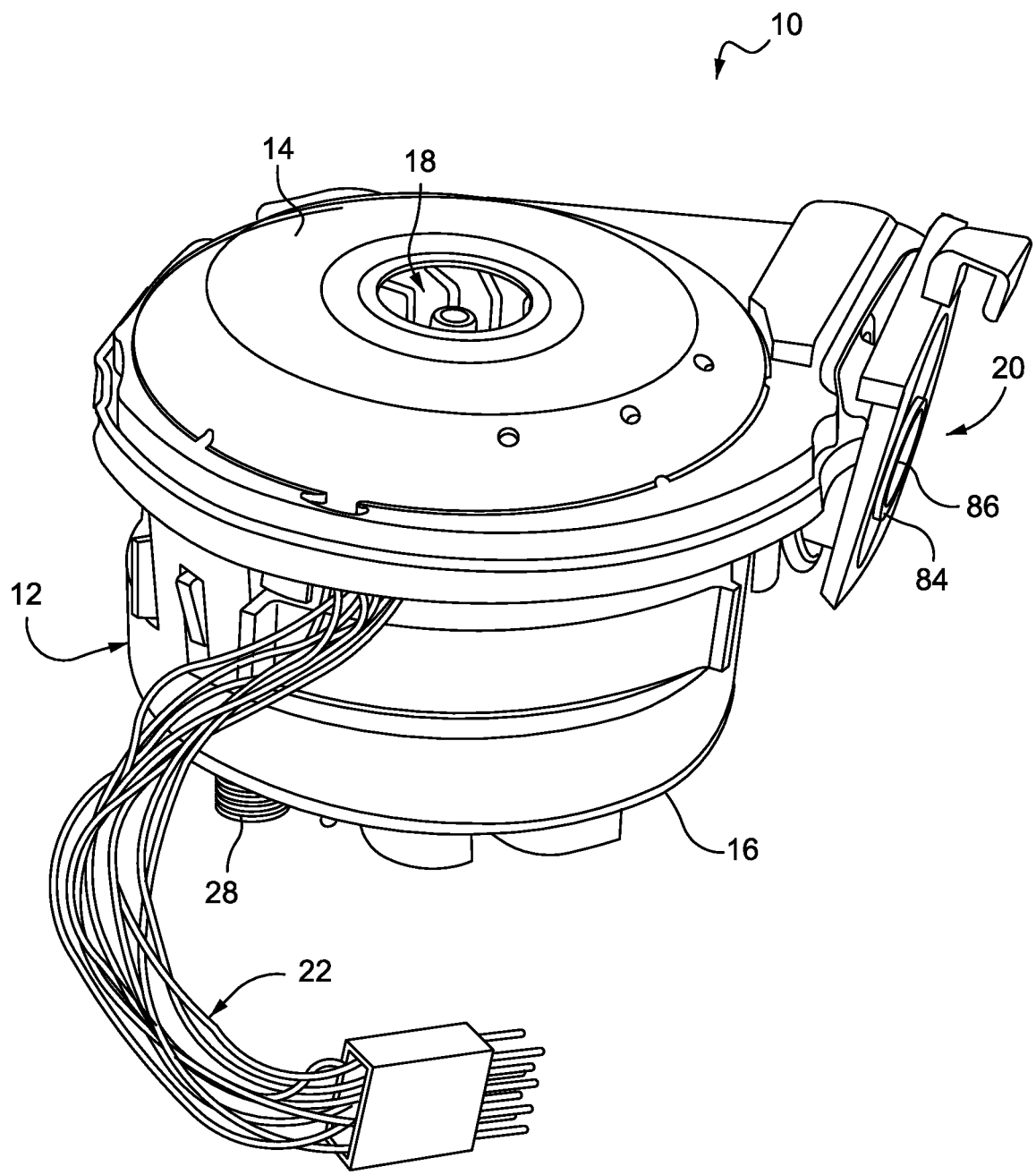
FIG. 2 is a perspective view of the blower motor assembly of FIG. 1, but rotated in a counter-clockwise direction about, a vertical center axis of the assembly approximately 90°.
Figure 3:
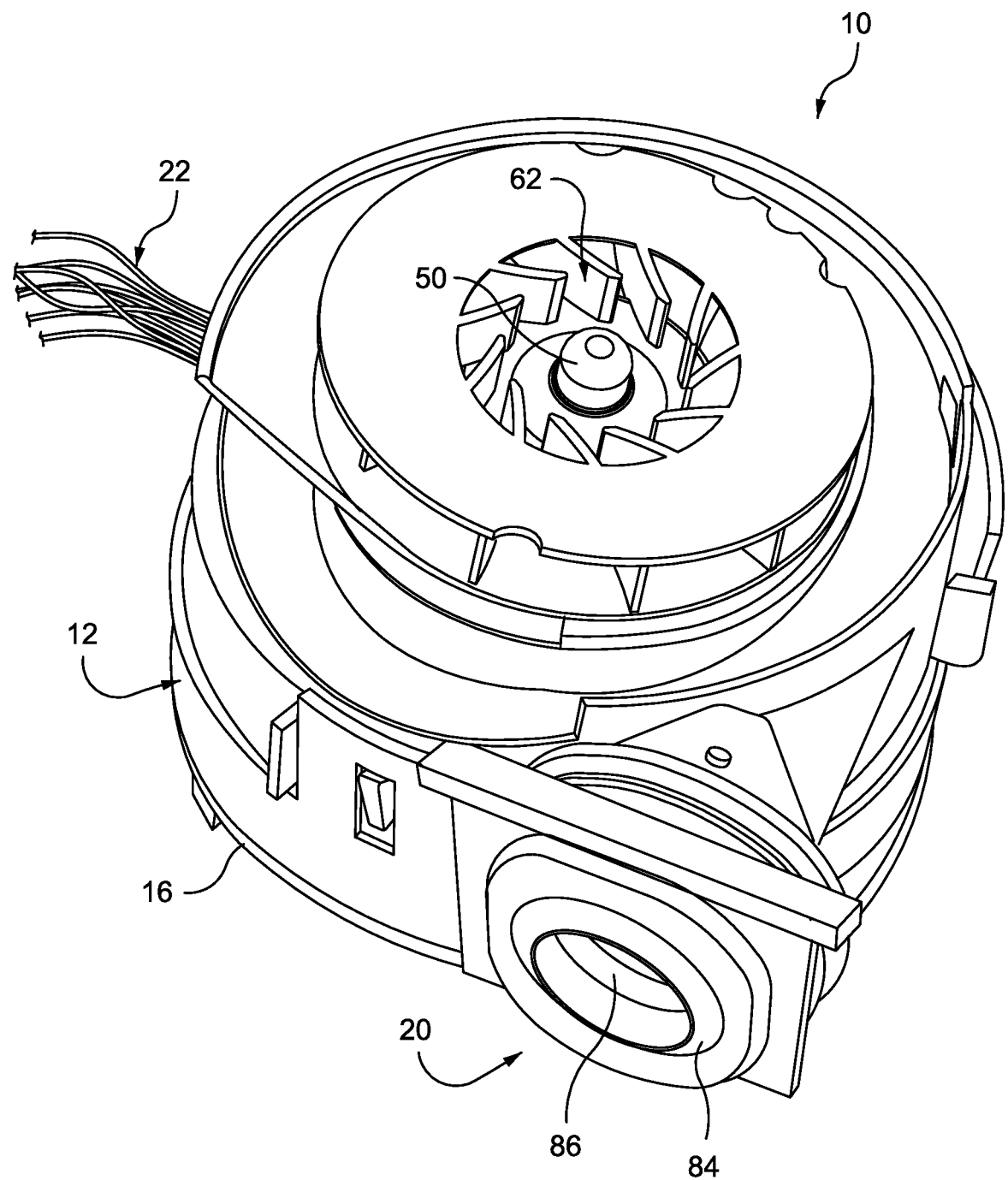
FIG. 3 is another perspective view of the blower motor assembly as shown in FIG. 1, but with a top cover of the assembly removed.
Figure 4:
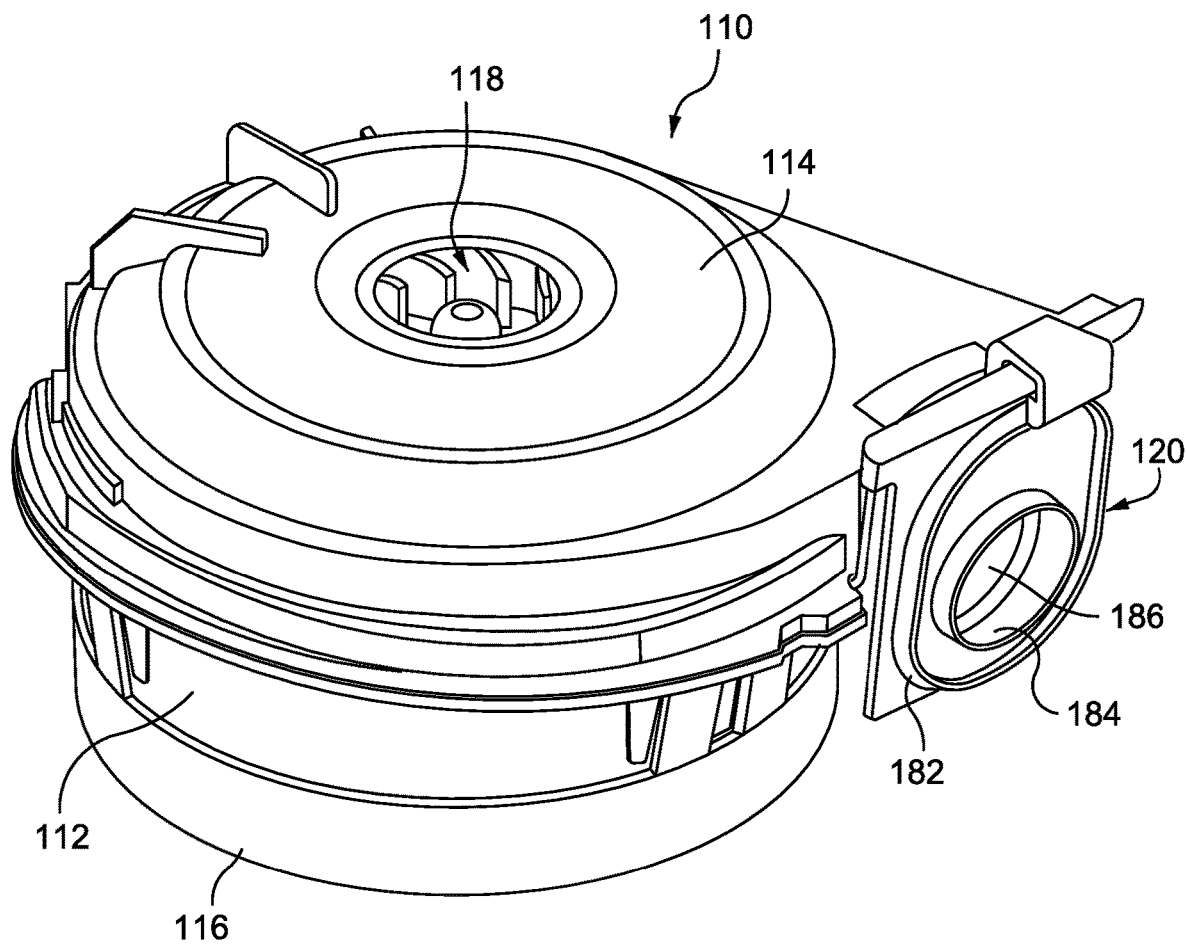
FIG. 4 is a perspective view of a blower motor assembly in accordance with another exemplary embodiment of the invention.
Figure 5:
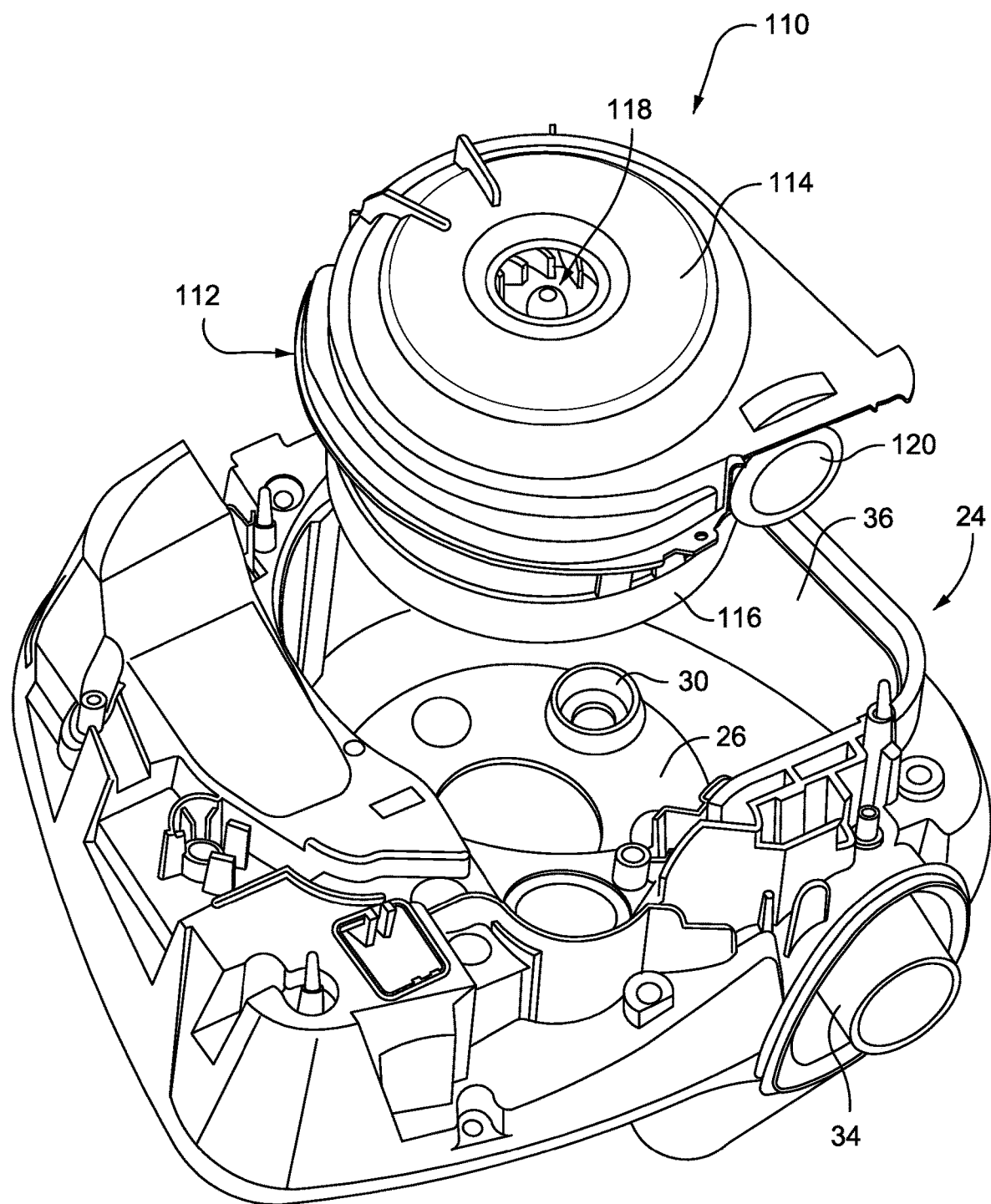
FIG. 5 is a an exploded perspective view illustrating the blower motor assembly of FIG. 4 in combination with a chassis.

Referring initially to FIGS. 1, 2 and 3, a blower motor assembly 10 in accordance with an exemplary embodiment generally includes a motor body 12 having a top cover 14 and a bottom cover 16. The motor itself is of conventional design and therefore need not be described in detail, other than to note that an output shaft (represented by center axis 48 in FIG. 7) projects from opposite upper and lower ends of the motor but does not extend through the top and bottom covers 14, 16 of the assembly. In this regard, it should be understood that references herein to terms such as "upper," "lower," "top" and "bottom," etc. are for convenience only as viewed in connection with the drawings, and are not intended to be limiting in any way.

A gas inlet opening 18 is provided in the top cover 14 and a gas outlet 20 is provided in a side wall of the motor housing 12. A power cable 22 extends from the motor body for connection to a power source.

Before describing the blower motor assembly 10 in detail, reference is made to FIGS. 5-7 and 11-14 that illustrate a chassis enclosure (or simply, chassis) 24 that is adapted to receive the blower motor assembly 10. More details of the chassis 24 can be found in U.S. patent application Ser. No. 10/533,840, filed May 4, 2005, incorporated herein by reference in its entirety. More specifically, the blower motor assembly may be supported on a bottom wall 26 of the chassis 24 via a plurality of coil springs 28 (one shown in FIGS. 1, 2). Three such springs are employed in the exemplary embodiment but the number and arrangement of such springs may vary. Springs 28 are seated in pockets or recesses 30 (see FIGS. 5 and 14) formed in the bottom wall 26 of the chassis 24, with the upper ends of the springs engaged in aligned similar pockets or recesses 31 in the underside of the bottom cover 16 of the blower motor assembly 10 (see FIG. 15).

A gas inlet conduit 32 in chassis 24 (see FIG. 7) supplies gas to the blower motor assembly 10, while gas outlet tube 34 connects to the gas outlet opening 20 of the blower motor assembly 10 when the latter is fully seated in the chassis.

Figure 11:
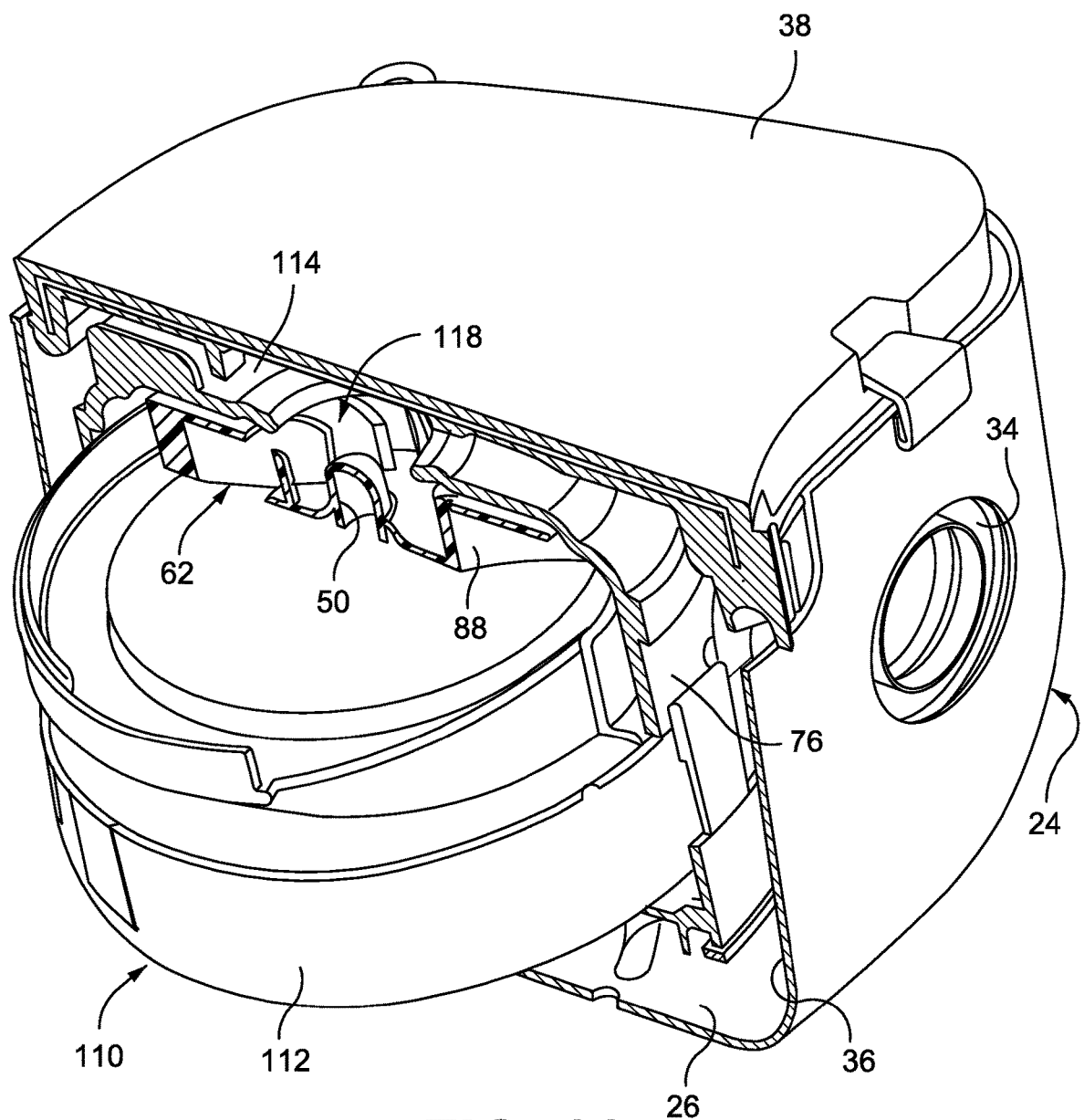
FIG. 11 is a perspective view, partially in section, of the blower motor assembly and chassis, similar to FIG. 6 but with a top lid placed over the chassis, and with part of the chassis and first stage impeller removed.
Figure 12:
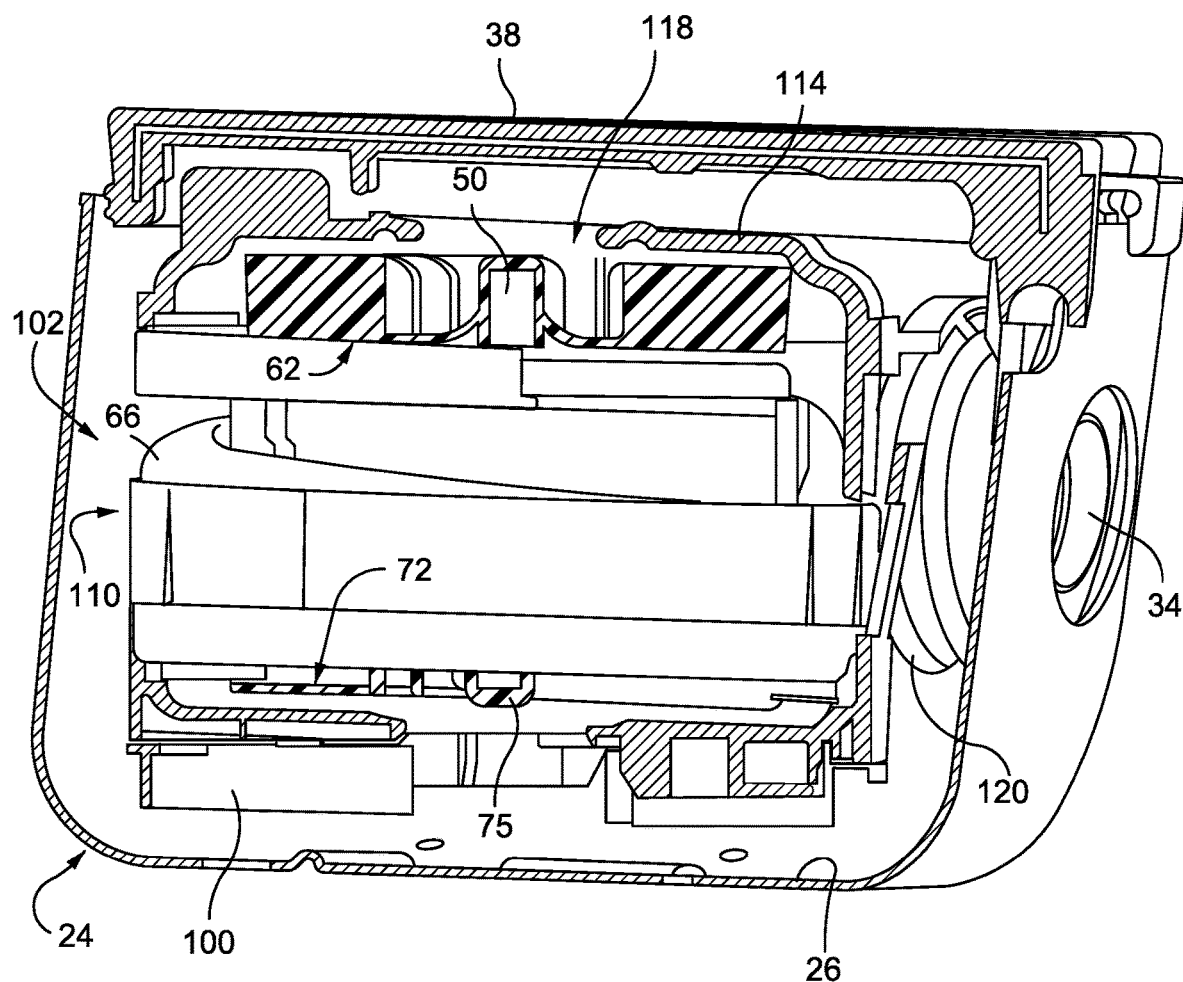
FIG. 12 is a view of the blower motor assembly and chassis of FIG. 11, but from a slightly different perspective, and with supporting springs removed for clarity sake.
Figure 13:
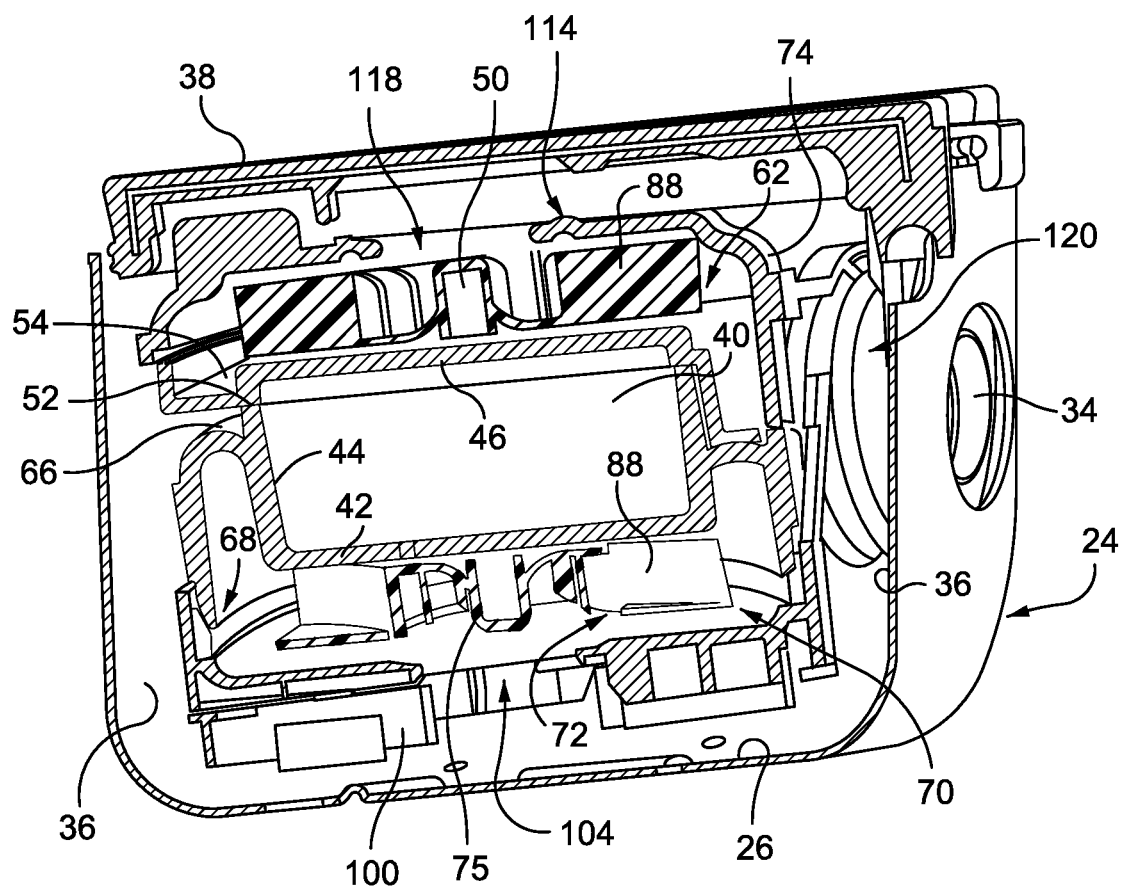
FIG. 13 is a sectional view similar to FIG. 12 but with the blower motor assembly sectioned as well.
Figure 14:
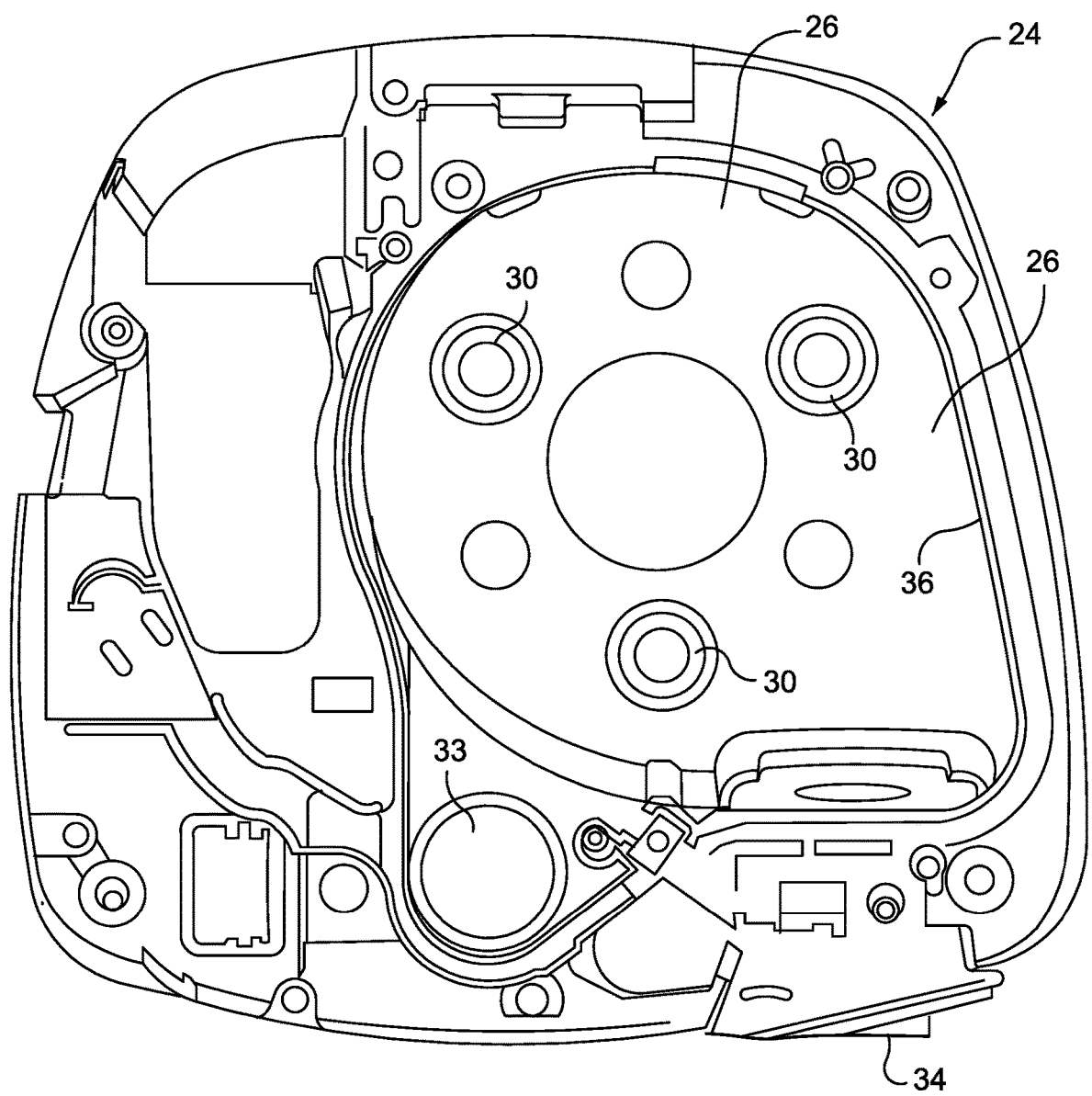
FIG. 14 is a plan view of the chassis, with the chassis lid and blower motor assembly removed.

The blower motor assembly 10 is preferably not enclosed within a typical outer motor enclosure or housing. As a result, the blower motor body 12 (FIGS. 1-3) itself is able to be installed within a smaller chassis, while maintaining a necessary gap between the motor body 12 and the peripheral side wall 36 of the chassis 24 for establishing the first-to-second stage gas path (as explained in further detail below). Note that wall 36 of the chassis 24 may be of double-wall construction (FIG. 7) or of single-wall construction (FIGS. 11-13). By supporting the blower motor assembly 10 on springs 28 (or other suitable vibration damping components), and spaced from the peripheral side wall 36 and lid 38 of the chassis, the blower motor is vibrationally isolated from the chassis 24.

Upon insertion of the blower motor assembly 10 into the chassis 24, a chassis lid 38 (FIGS. 7 and 11-13) is located over the blower motor assembly, closing the upper open end of the chassis.

With this general description in mind, the components as well as the operation of the device will now be described in greater detail.

b) Blower Motor Assembly

It should be noted here that the blower motor assembly 10 shown in FIGS. 1-3 is slightly different from the blower motor assembly 110 of FIGS. 4-7 and 11-14. The assembly shown in FIGS. 1-3 is shown with various details, some of which are related to manufacturing considerations that may or may not appear in the assembly shown in FIGS. 4-7 and 11-14 and vice versa, particularly with respect to the blower motor body, top cover and bottom cover. In this regard, the external component of the blower motor assembly in FIGS. 4-7 and 11-14 are designated by similar reference numbers as used in FIGS. 1-3, but with the prefix "1" added. To this extent, assemblies 10 and 110 may be considered different embodiments although they are similar in terms of overall configuration and function. In addition, and, for purposes of this disclosure, the internal components of blower motor assemblies 10 and 110 should be considered substantially identical.

With particular reference to FIGS. 7 and 11-13, the blower motor assembly 110 includes a motor body 112 formed with an interior chamber 40 defined by a bottom wall 42 of the body 112, an inner side wall 44 and a motor cap or end bell 46. The motor coil and armature (omitted for clarity) are secured within the motor body 112 in conventional fashion and an output shaft, shown schematically at 48, extends in opposite directions through the motor cap 46 and the bottom wall 42 of the body 112. The cap 48 and the bottom wall 42 may include suitable bearing supports for the shaft. Note that the motor cap 46 engages an upper peripheral edge 52 of the motor body 112 and, via lateral flange 54 and vertical lip 56, engages an internal shoulder 58 of the top cover 114. The space 60 (also referred to herein as the "first volute") between the motor cap 46 and the blower motor assembly top cover 114 is occupied by the first stage impeller 62 that is secured to the upper end of the motor output shaft 48 via a center hub or bushing 50.

The blower motor body 112 is also formed with a depending skirt or outer wall 64 that is connected at its upper end to the inner side wall 44 by a generally horizontal flange 66. The flange 66 and thus the upper end of the outer wall 64 spirals downwardly about the inner side wall 44, forming the second stage volute (described further herein)—while the lower end of the outer wall 64 is engaged by the blower motor assembly bottom cover 116 by a telescoping fit indicated at 68. The space 70 (also referred to herein as the "second volute") between the bottom cover 116 and the bottom wall 42 of the blower motor body 112 is occupied by a second stage impeller 72 that is secured to the lower end of the motor output shaft 48 via a center hub or bushing 75. The blower motor body 112 and cap 46 are preferably made of aluminum or other suitable heat conducting material for good thermal conduction, such as magnesium. The heat conducting material can help to convectively cool the motor and has good heat transfer characteristics. In addition, the heat taken away from the motor can be applied to heat the pressurized gas traveling to the patient, e.g., via the air delivery tube. Alternatively, the heat can simply be diverted away from the motor and the air delivery tube.

The top cover 114 of the blower motor assembly includes upper and lower portions 74, 76, respectively. The upper portion may be constructed of a relatively rigid plastic or other suitable lightweight material and has a generally inverted cup-shape, with a center opening or aperture 118 through which air is supplied to the first stage impeller 62. The lower portion 76 of the top cover is in the form of a depending skirt, attached to the upper portion 74 adjacent the shoulder or edge 58 by adhesive or any other suitable means. The lower portion 76 is preferably constructed of a flexible polymer or rubber material (e.g., silicone rubber) that enables the top cover 114 to seal against the inner peripheral wall 36 of the chassis 24 at 78. The significance of this sealing arrangement will be described further below.

The gas outlets 20 and 120, respectively, of the blower motor assemblies 10 and 110 are also formed of a flexible material, such as silicone rubber. This results in a flexible sealed connection to the chassis gas outlet tube 34 when the blower motor assemblies 10 or 110 are inserted and properly oriented within the chassis 24. The gas outlets 20, 120 each include an outer oval-shaped peripheral rim 82, 182 and an inner, round rim 84, 184 define the outlet openings 86, 186 and that, respectively, are adapted to engage complimentary surfaces on the inner wall of the chassis 24, with rims 84, 184 specifically designed to be sealably engaged by the round outlet tube 34 of the chassis.

c) Impellers c1) First Embodiment—Alternating Double Shroud Impeller

Figure 8:
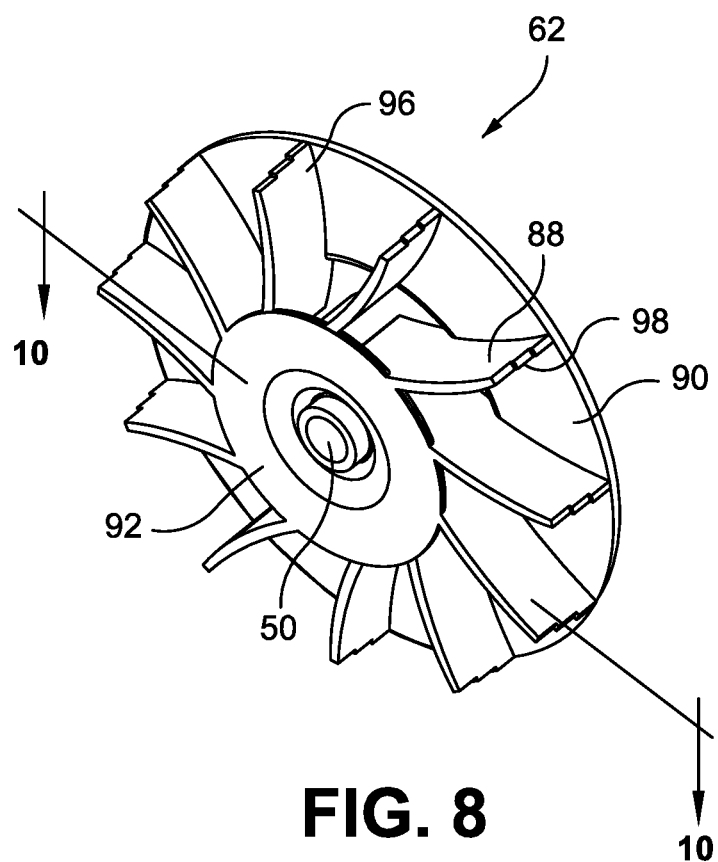
FIG. 8 is a perspective view of an impeller of the kind incorporated into the blower motor assemblies shown in FIGS. 1 and 4.
Figure 9:
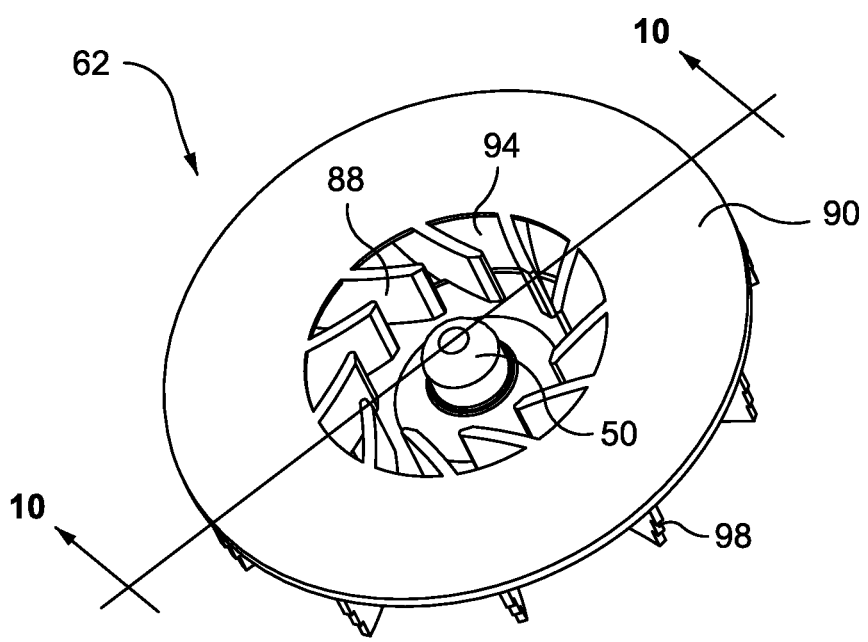
FIG. 9 is a perspective view of the opposite side of the impeller shown in FIG. 8.
Figure 10:
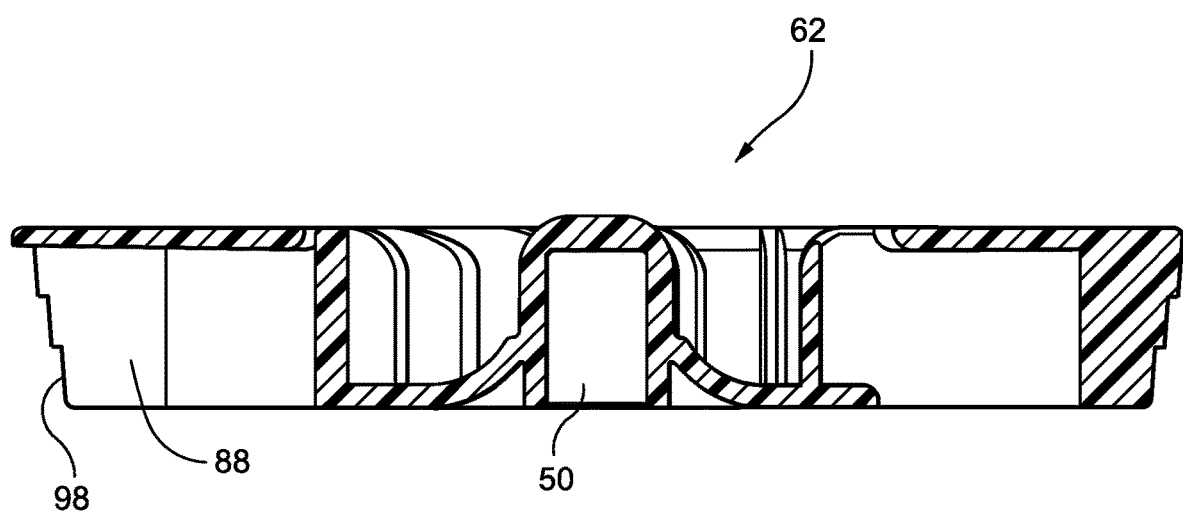
FIG. 10 is a section taken through line 10-10 of FIG. 9.
Figures 1, 10:
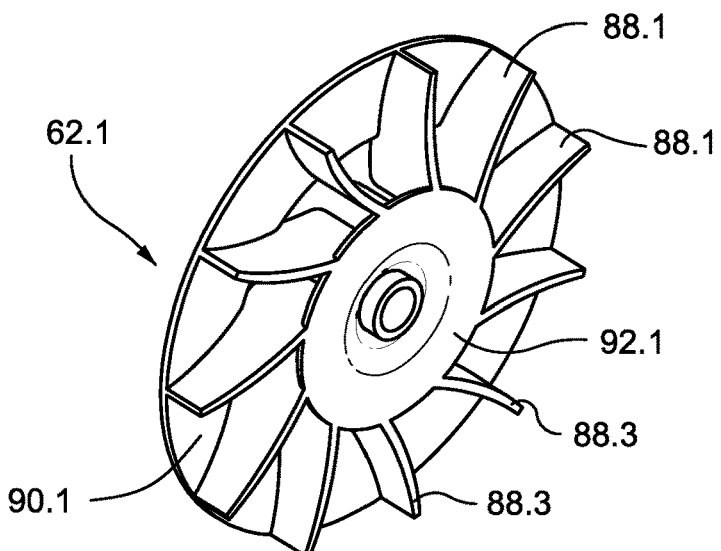
Figures 2, 10:
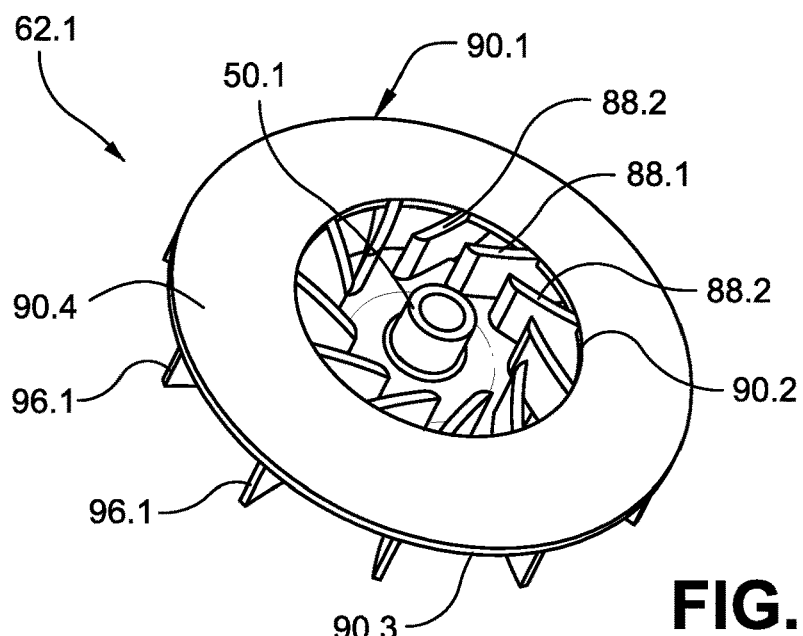
Figures 3, 10:
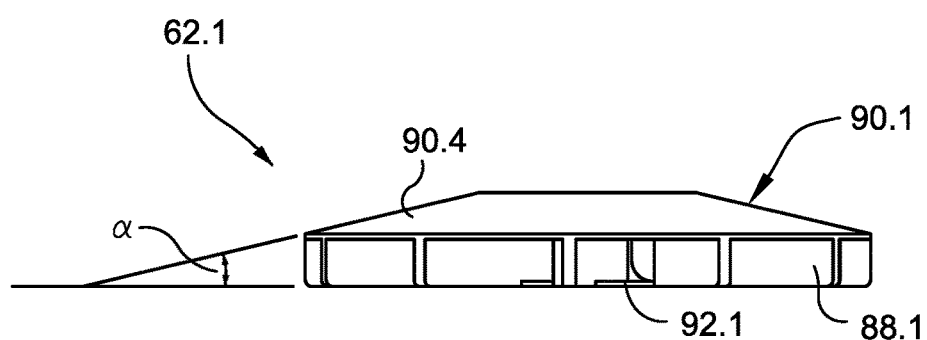
Figures 4, 10:
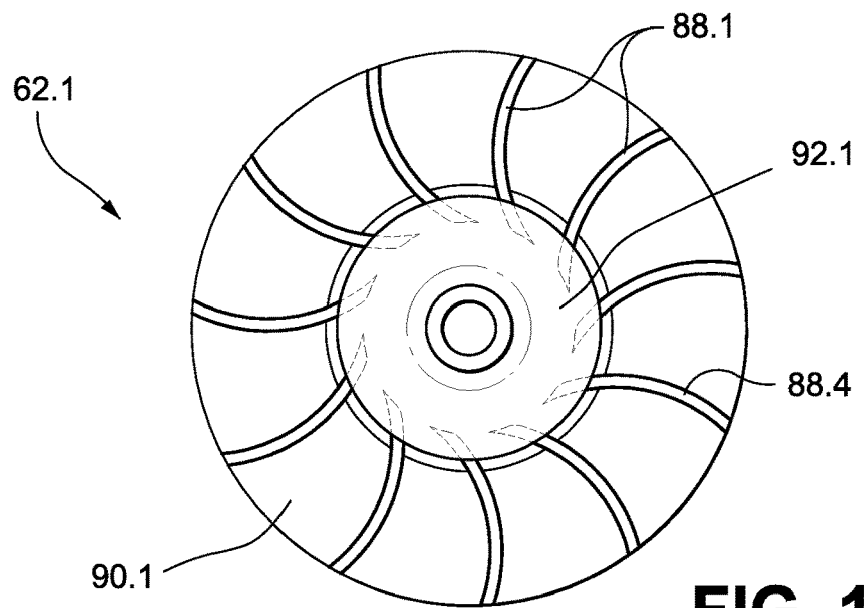
Figures 5, 10:
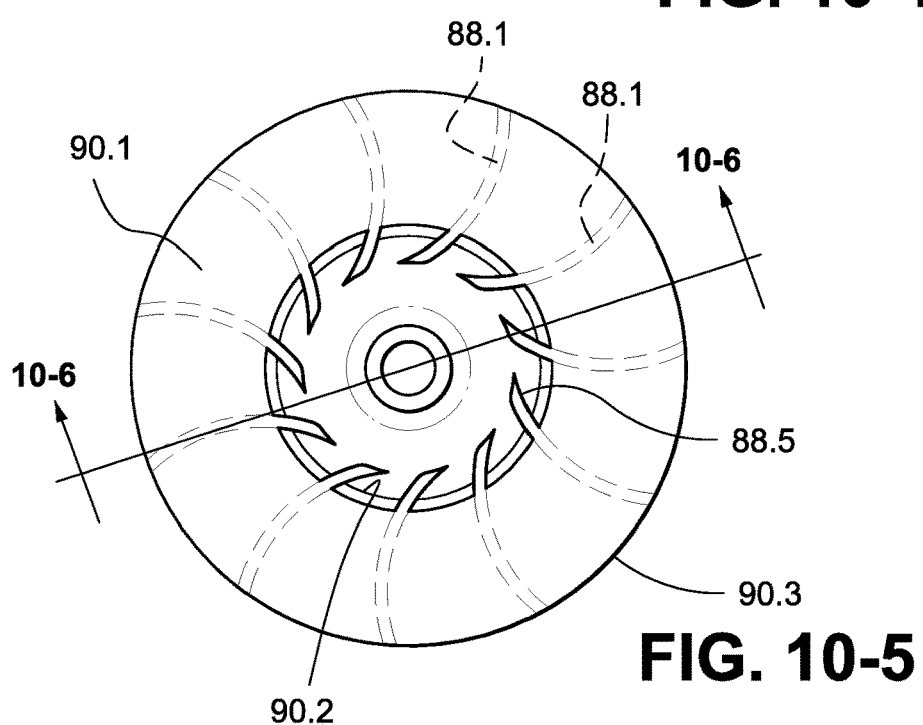
Figures 6, 10:
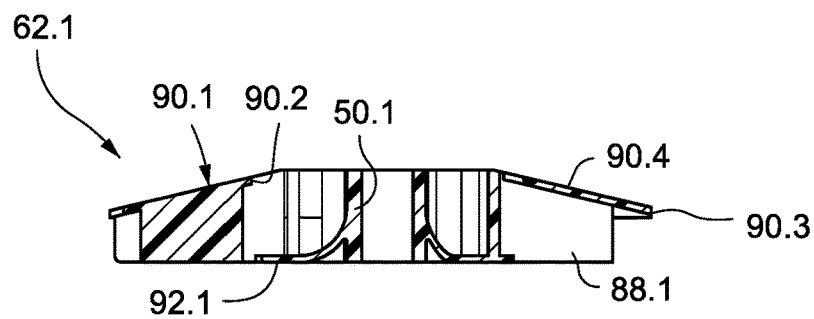
Figures 9, 10:
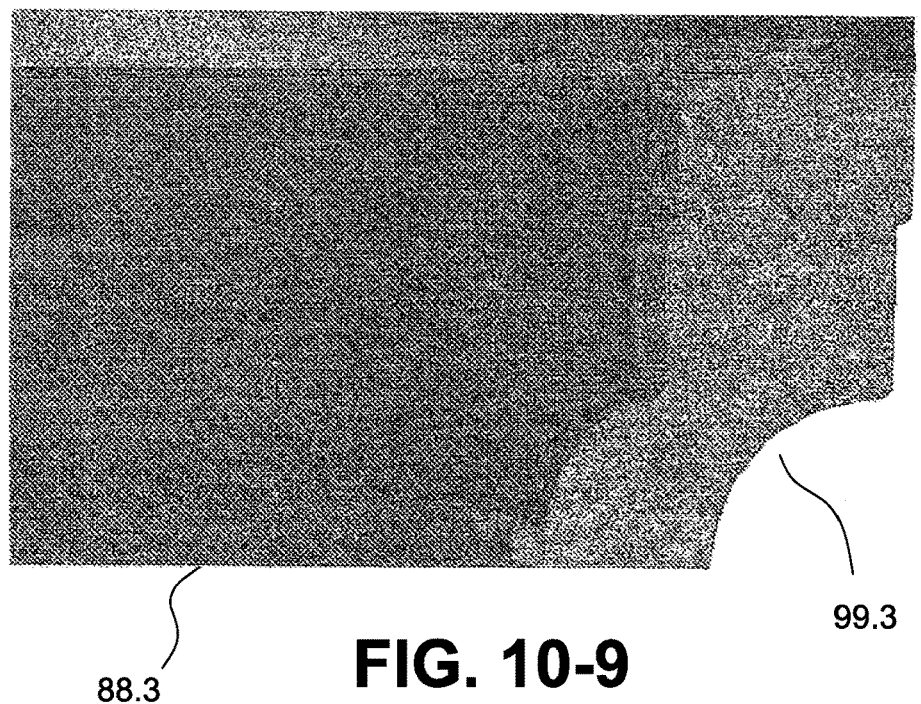
Figure 10:
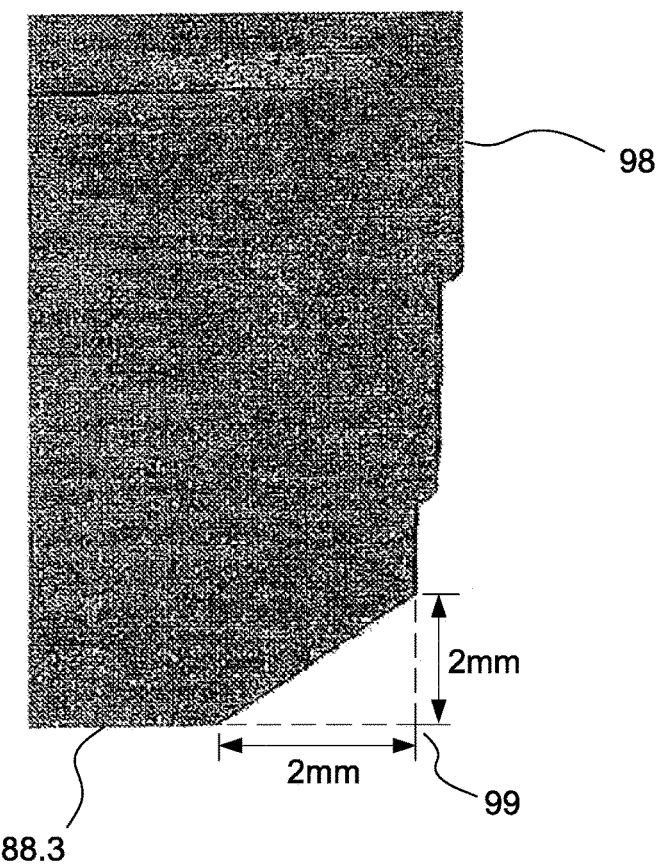

The first and second stage impellers 62, 72 may be identical in design (though must be of mirrored geometry to suit the present embodiment) and, accordingly, only the impeller 62 will be described in detail. With particular reference to FIGS. 8-10, impeller 62 is of one-piece molded plastic construction, although other suitable materials and manufacturing techniques could be employed. The impeller 62 comprises a plurality of continuously curved or straight vanes or blades 88 sandwiched between a pair of disk-like shrouds 90, 92. The smaller shroud 92 incorporates the hub or bushing 50 that receives the upper end of the motor shaft 48. The shroud 92 overlaps an inner portion of the vanes 88, i.e., the outer diameter (OD) of the smaller shroud is substantially smaller than the OD of the larger shroud 90. The latter is formed with a relatively large center opening 94, but this shroud extends to the radially outer tips of the vanes. Making the OD of the smaller shroud 92 slightly smaller than the diameter of the center opening 94 in shroud 90, facilitates the molding process used to manufacture the impellers (by allowing the impeller to be easily moulded in one piece).

By utilizing the differentially sized shrouds (specifically by having only one shroud in the outer portion of the impeller), the inertia of the impellers 62, 70 is reduced while the overall rigidity of the impellers is maintained. In this regard, both impellers 62, 72 are preferably constructed of a polycarbonate or polypropylene material (the latter of which provides acoustic dampening properties that dampen the resonance of the impellers). Glass fibre reinforcement may be employed to increase the stiffness of the polypropylene or polycarbonate if required.

The radially outer portions 96 of the vanes or blades 88 taper in width and the transverse tip edges 98 may be stepped, as best seen in FIG. 10. Each vane may have a profile appropriate for the intended goal and such profile may be tapered. For example, each vane may taper in plan view (i.e., the edge thickness of each vane may taper from a larger width to a narrower width from inside to outside), and/or each vane may taper in elevation view (i.e., the height of each vane along the length may taper from a larger height to a smaller height from inside to outside). This may be achieved by tapering the vane or blade edges adjacent the smaller-diameter shroud so that at least the radially outer portion of the blade tapers to a reduced width at the radially outer end of the impeller. In addition, the cross-section thickness of the vanes may be variable or tapered. These vane features are intended to reduce noise, and the stepped specifically function to break up pressure pulses around the tips of the vanes. In alternative embodiment the trailing edges of the impeller blades may be disrupted by other disturbances, such as but not limited to dimpling or roughening. Such disturbances break up the smooth flow of air trailing off the blade edges and assist in reducing noise.

Figure 7:
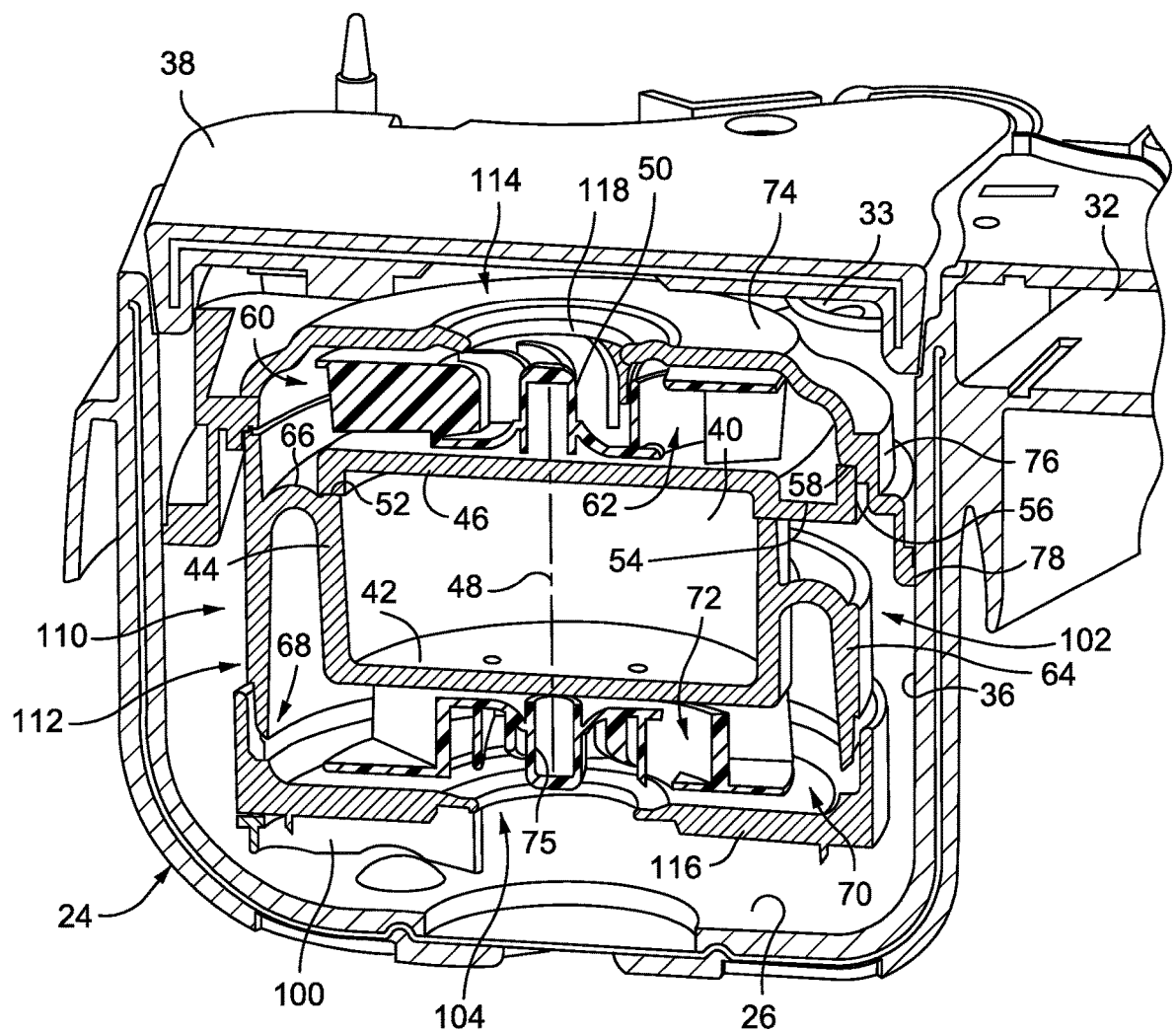
FIG. 7 is a cross-section taken along the line 7-7 of FIG. 6.

In one embodiment, illustrated in FIGS. 10-7 to 10-9, the tip of the impellers between the edge surface 88.3 which extends beyond the smaller shroud 92 and the transverse tip edges 98 is chamfered or notched to create a transition surface 99 at the tip. Examples of this transition surface include a straight chamfer 99.1 (FIGS. 10-7), a convex chamfer, for example arcuate 99.2 (FIG. 10-8), or a concave notch 99.3 (FIGS. 10-9).

The chamfer or notch dimension is preferably between 0.5-5 mm along each edge (98 and 88.3), more preferably about 2 mm, from the notional corner that is formed by extending the planes of the transverse tip edges 98 and the edge surfaces 88.3 to intersect, as shown in FIG. 10-10. The dimension along each edge is not required to be the same.

The chamfering or notching of the blade as described is intended to further reduce noise, including decreasing the blade passing tones.

Figure 15:
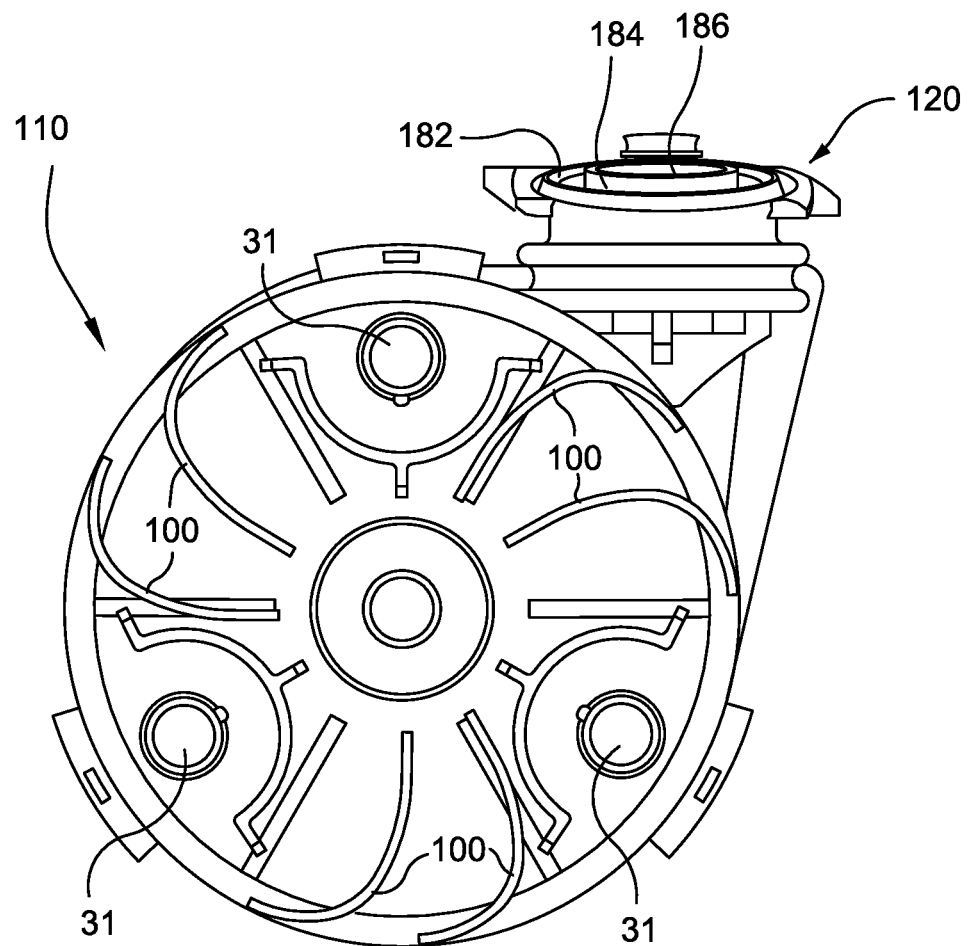
FIG. 15 is a bottom plan view of the blower motor assembly shown in FIG. 4.
Figure 16:
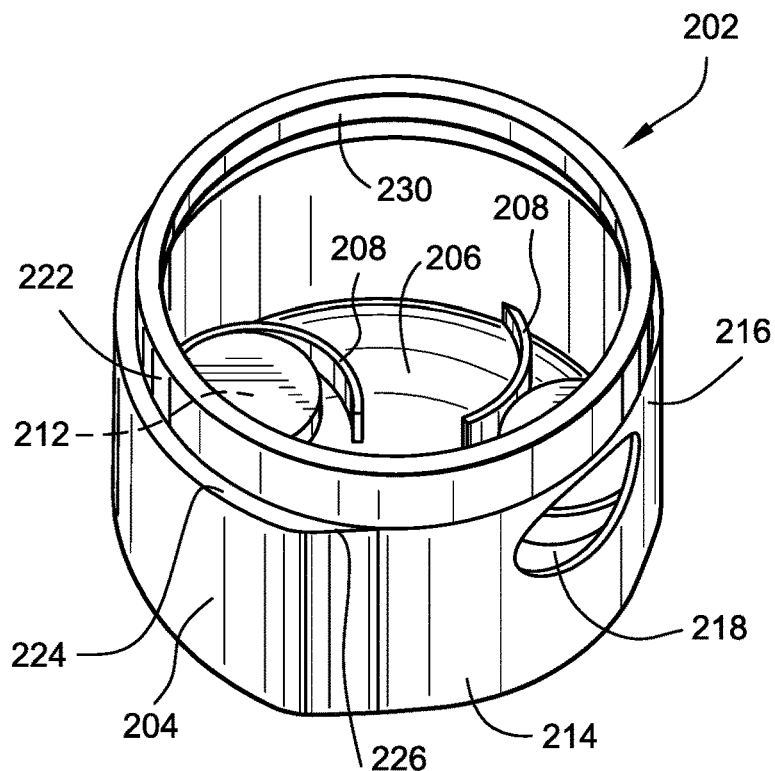
FIG. 16 is a perspective view of a flexible sleeve for use with a blower motor assembly in accordance with another embodiment.
Figure 17:
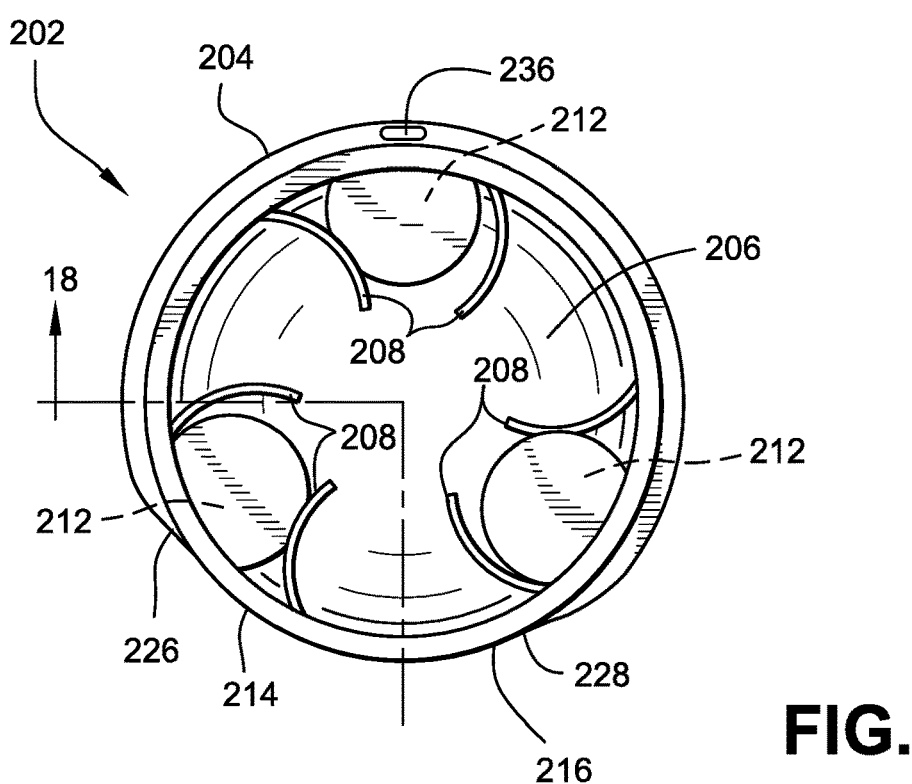
FIG. 17 is a top plan view of the sleeve shown in FIG. 16.
Figure 18:
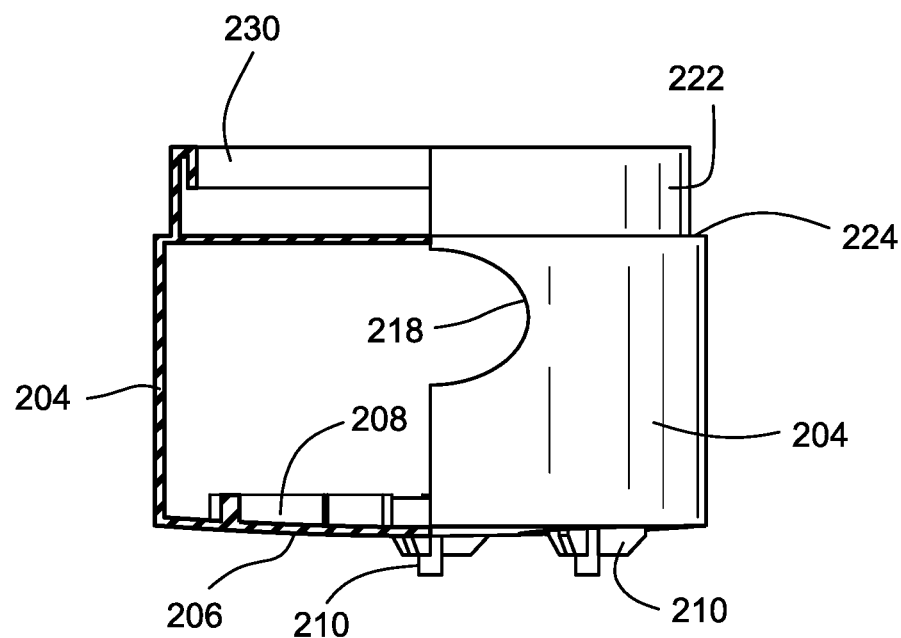
FIG. 18 is a side elevation of the sleeve shown in FIG. 17, sectioned along line 18.
Figure 19:
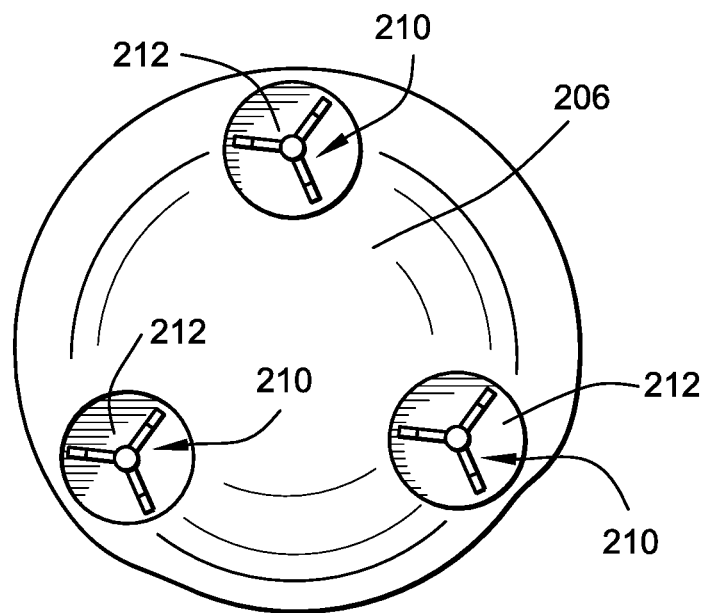
FIG. 19 is a bottom plan view of the sleeve shown in FIG. 16.

The exterior or outer surfaces of the bottom covers 16, 116 are also provided with a plurality of fixed vanes 100 that may be arranged in three sets of two as shown in FIG. 15, but other arrangements are contemplated as well. These vanes serve to reduce the degree of swirl or spin of the gas before it flows gas into the second stage impeller 72 as further described herein.

c2) Second Embodiment—Tapered, Alternating Double Shroud Impeller

Figure 6:
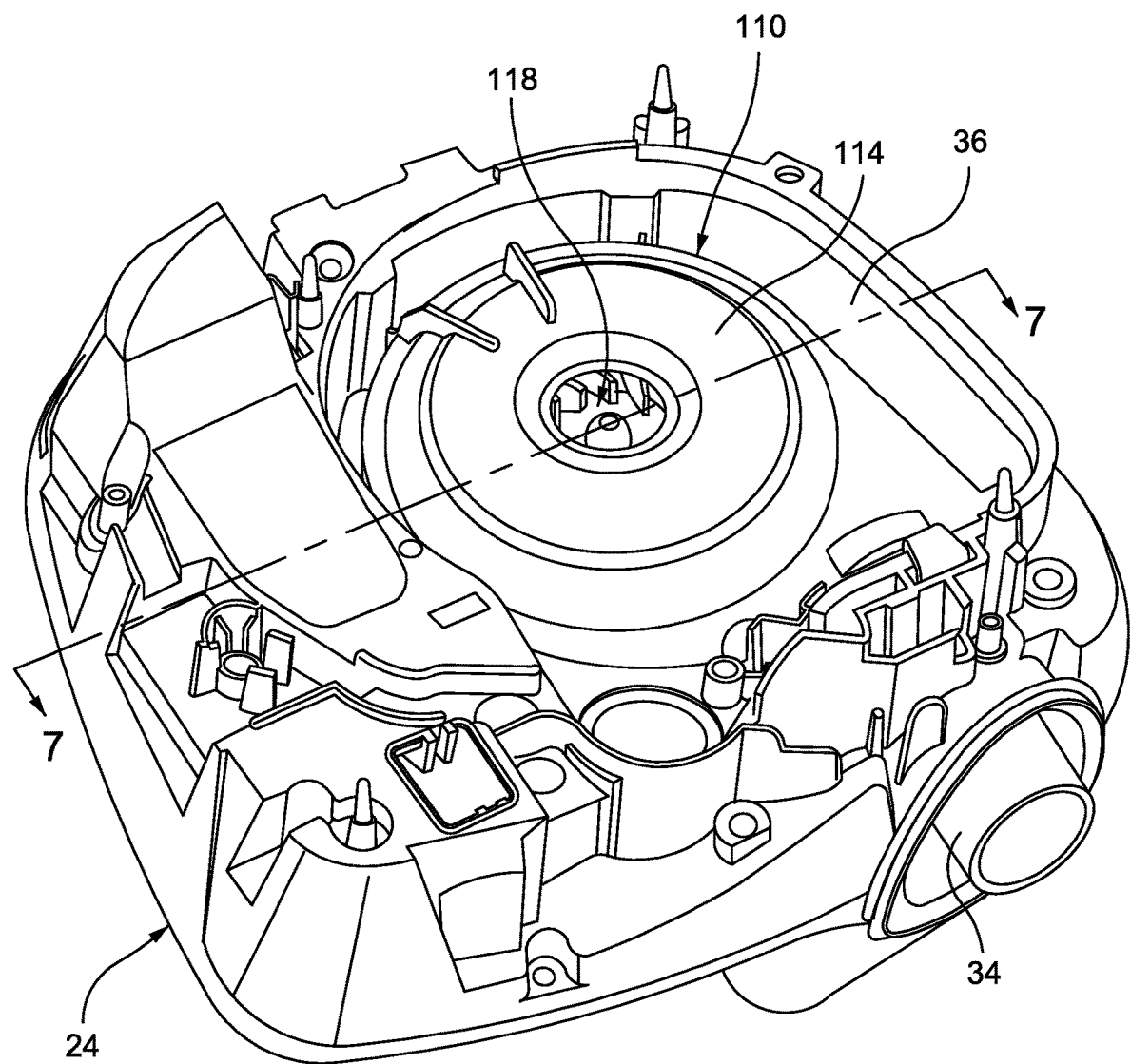
FIG. 6 is a perspective view similar to FIG. 5, but with the blower motor assembly inserted within the chassis.

FIGS. 10-1 to 10-6 illustrate an impeller 62.1 according to an alternative design of the present invention. Like impeller 62 shown in FIGS. 8-10, impeller 62.1 includes an alternating shroud design, but in addition it is tapered in elevation view, e.g., the height of each vane varies or tapers along its radial length as shown, for example, in FIGS. 10-1 and 10-6. Each vane may also be tapered in widthwise direction, as seen in plan view. This tapered alternating shroud impeller combines the advantages of an alternating shroud impeller (lower costs, lower inertia and better balance) with the advantages of a tapered impeller (more uniform radial air velocity through the impeller and hence lower noise and higher efficiency). As a side benefit, the tapered alternating shroud design also provides excellent stiffness and resistance to bending, drooping, or "creep".

As noted above, impeller 62.1 has a tapered design and includes a plurality of continuously curved or straight vanes or blades 88.1 sandwiched between a pair of disk-like shrouds 90.1, 92.1. Each vane 88.1 includes a first edge 88.2 and a second edge 88.3. The radially outer portion 88.4 (FIG. 10-4) of each edge 88.2 abuts or is in contact with or adjacent to an inside surface of shroud 90.1, while the radially inner portion 88.5 (FIG. 10-5) of the edge 88.2 of each vane extends further radially inwardly beyond shroud 90.1 and is visible through opening 90.2 (also referred to as the "small diameter" of shroud 92.1). Conversely, the radially inner portion of each edge 88.3 abuts or is in contact with or adjacent to an inside surface of shroud 92.1, while the radially outer portion of each edge 88.3 of each vane extends further radially outwards beyond shroud 92.1. and is visible in FIG. 10-1. The tapered design is created in this example by forming shroud 90.1 in a truncated frustoconical shape, while shroud 92.1 is generally planar (see FIG. 10-6). The vanes 88.1 between the shrouds are shaped to fit in the space between the shrouds, such that the vanes gradually taper from the radially inner portion to the radially outer portion of the impeller along the larger-diameter shroud.

The small and large diameters 90.2, 90.3, respectively, of the truncated cone form a slanted wall 90.4 that is angled relative to shroud 92.1. The angle α is in the range of 0-60°, preferably between 10-30°, depending on the application. By contrast, the shrouds in FIGS. 8-10 extend in generally parallel planes, although they may be of varying thickness. The smaller shroud 92.1 incorporates the hub or bushing 50.1 that receives the upper end of the motor shaft 48. The shroud 92.1 overlaps an inner portion of the vanes 88.1, i.e., the outer diameter (OD) of the smaller shroud 92.1 is substantially smaller than the OD of the larger shroud 90.1. Shroud 90.1 is formed with opening 90.2 that does not cover the radially inner portions of the vanes, but shroud 90.1 extends to the radially outer tips of the vanes. Making the OD of the smaller shroud 92.1 slightly smaller than the diameter of the center opening 90.2 in shroud 90.1, facilitates the molding process used to manufacture the impellers.

By utilizing the differentially sized shrouds (specifically by having only one shroud in the outer portion of the impeller), the inertia of the impellers 62.1 is reduced while the overall rigidity of the impellers is maintained. In this regard, impeller 62.1 is preferably constructed of a polycarbonate or polypropylene material which provides acoustic dampening properties (the latter of which dampens the resonance of the impellers). Glass fiber reinforcement may be employed to increase the stiffness of the polypropylene or polycarbonate if required.

The radially outer portions 96.1 of the vanes or blades 88.1 may taper in width and the transverse tip edges 98.1 may be stepped, similar to what is shown in FIG. 10-6 and/or notched or chamfered 99 as shown in FIGS. 10-7 to 10-10 and described above.

These vane features are intended to reduce noise, and stepped edges specifically function to break up pressure pulses around the tips of the vanes. In alternative embodiment the trailing edges of the impeller blades may be disrupted by other disturbances, such as but not limited to dimpling or roughening. Such disturbances break up the smooth flow of air trailing off the blade edges and assist in reducing noise.

Impeller 62.1 is also strong (higher rpms possible) and is even lower inertia (faster response) and possibly quieter than impeller 62, which is a generally parallel arrangement. Further, impeller 62.1 can be made in one piece due to its design.

The tapered alternating shroud embodiment is low cost and has good balance, very low inertia, low noise, and high strength. The use of a tapered, shrouded design also involves less material usage. The tapered design can also result in more even gas velocity, e.g., velocity is kept constant between the radially inner and outer ends of the vanes.

The gap between the top of the impeller and the top cover of a double shrouded impeller is not as sensitive to tolerances, compared to a single shroud impeller. On single shrouded (or open) impellers, the top gap is very sensitive to variation, as the air can spill over the top of the blade if the top cover is relatively far away.

d) Volutes

Returning to FIGS. 7 and 11-13, it will be seen that the first volute is defined by the space 60 (enclosing the first stage impeller 62 and also including an annular volute region immediately outward of the impeller) which is formed by the underside of the top cover 114 and the upper (or outer) side of the motor cap 46. After leaving the first volute 60 (a high velocity region), the air follows an inter-stage (i.e., a stage-to-stage) path 102 which is a radially outer, downward spiral path in the area between the outer peripheral skirt 64 of the blower motor body 112 and the inner wall 36 of the chassis 24 leading to an inlet opening 104 in the blower motor body bottom cover 116. This inlet opening feeds the air pressurized by the first impeller 62 within the first volute 60 and transferred to the second stage impeller 72 and the second volute 70 via the inter-stage (stage-to-stage) path 102, with the gas flow into the opening 104 smoothed (deswirled) by vanes 100.

The second volute, as noted above, is defined by the chamber or space 70 enclosing the second stage impeller 72 and continuing in an upward spiral path between the outer and inner walls 64, 44, respectively, of the motor housing, leading to the gas outlet 20, 120.

It will be appreciated that having the inter-stage (stage-to-stage) path 102 nested concentrically outside the first volute 60 and the second volute 70 provides considerable savings in the overall size of the blower motor assembly, thus enabling it to be installed in a smaller chassis.

The first and second volutes may have similar or different shapes. However, the first volute can be said to "ramp down", while the second volute can be said to "ramp up". Each ramp profile is preferably smooth, but each can also have a stepped gradient as well.

e) Operation

In operation, and using the embodiment or FIGS. 4-15 as an example, gas, typically air or oxygen, is supplied to the blower motor assembly 110 via conduit 32 and hole 33. The air is then drawn in through inlet opening 118 and into the first stage impeller 62. The impeller spins the gas and, in combination with the first volute 60 pressurizes the gas. After decelerating as it leaves the first volute, it flows in a downward spiral on the inter-stage (stage-to-stage) path 102, moving into the space between the motor body 112 and the chassis wall 36. Note that the seal at 78 between the motor body top cover 114 and the chassis wall 36 prevents pressurized gas from escaping back into the nonpressurized area above the inlet opening 118. The flexible nature of the seal also contributes to the vibration isolation of the blower motor assembly relative to the chassis enclosure.

The gas, guided by fixed vanes 100, now flows into the second impeller 72 which, in combination with the second volute 70, further pressurizes the gas until it reaches the motor body assembly outlet 120 and exits via the chassis outlet tube 34.

While the blower described herein can be used for use in CPAP, NIPPV and BiLevel treatment of OSA, it should noted that the blower could also easily be used or adapted for use with invasive ventilation as well.

f) Alternative Flexible Sleeve Embodiment

In an alternative arrangement, a blower motor assembly 200 (FIGS. 20, 21), similar to the assemblies described hereinabove, is substantially enclosed by a cup-shaped, flexible sleeve 202, best seen in FIGS. 16-19. The sleeve 202 includes a peripheral side wall 204 and a bottom wall 206. The bottom wall 206 of the sleeve may be formed with internal curved vanes 208 that surround the second stage inlet opening of the blower motor assembly in a manner similar to the arrangement of vanes 100 described above.

Figure 22:
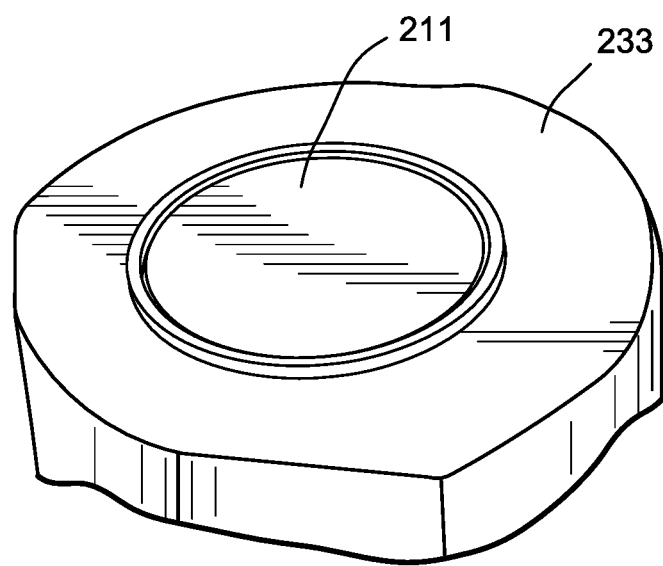
FIG. 22 is a partial perspective of a variation of the flexible sleeve shown in FIGS. 16-21.

The vanes 208 are preferably formed integrally with the bottom wall 206, but could be separately applied, if desired, by for example, a suitable adhesive. The vanes could also be formed on the underside of the blower motor assembly bottom cover as in the previously described embodiments. A plurality of support feet 210 are shown integrally molded within circular recesses 212 formed in the bottom wall 232. Another support arrangement could be one large cylindrical web 211 on the bottom outer face 233 of the sleeve, as shown in FIG. 22.

Figure 20:
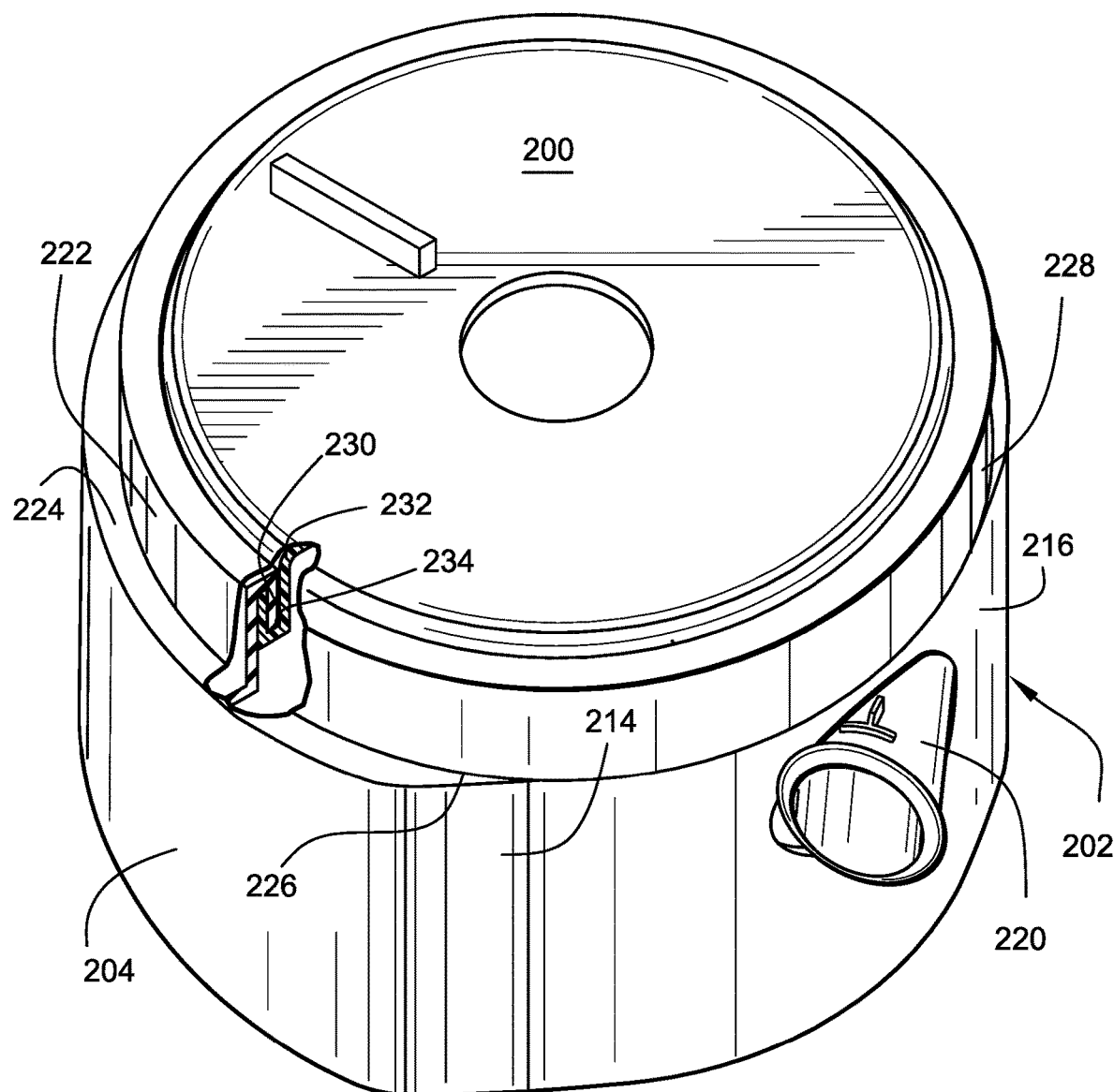
FIG. 20 is a perspective view, partially cut away, of the sleeve of FIG. 16 assembled over a blower motor assembly.

The peripheral side wall 204 of the sleeve 202 is substantially circular in cross-section, but with a pair of "flats" 214, 216 on either side of an aperture 218 adapted to receive the gas outlet connector boss 220 (see FIG. 20). The upper end of the sleeve may be formed with a reduced diameter portion defining an upper rim 222 connected to the adjacent remaining sleeve portion by a radial shoulder 224. Note that the rim 222 merges with the main portion of the sidewall 204 at the flats 214, 216 such that the shoulder 224 terminates at locations 226, 228. Rim 222 terminates at an internal, circular flange or lip 230 located radially inwardly of the rim 222. It will be appreciated that other equivalent attaching and/or sealing arrangements at the open end of the sleeve are within the scope of this invention.

Figure 21:
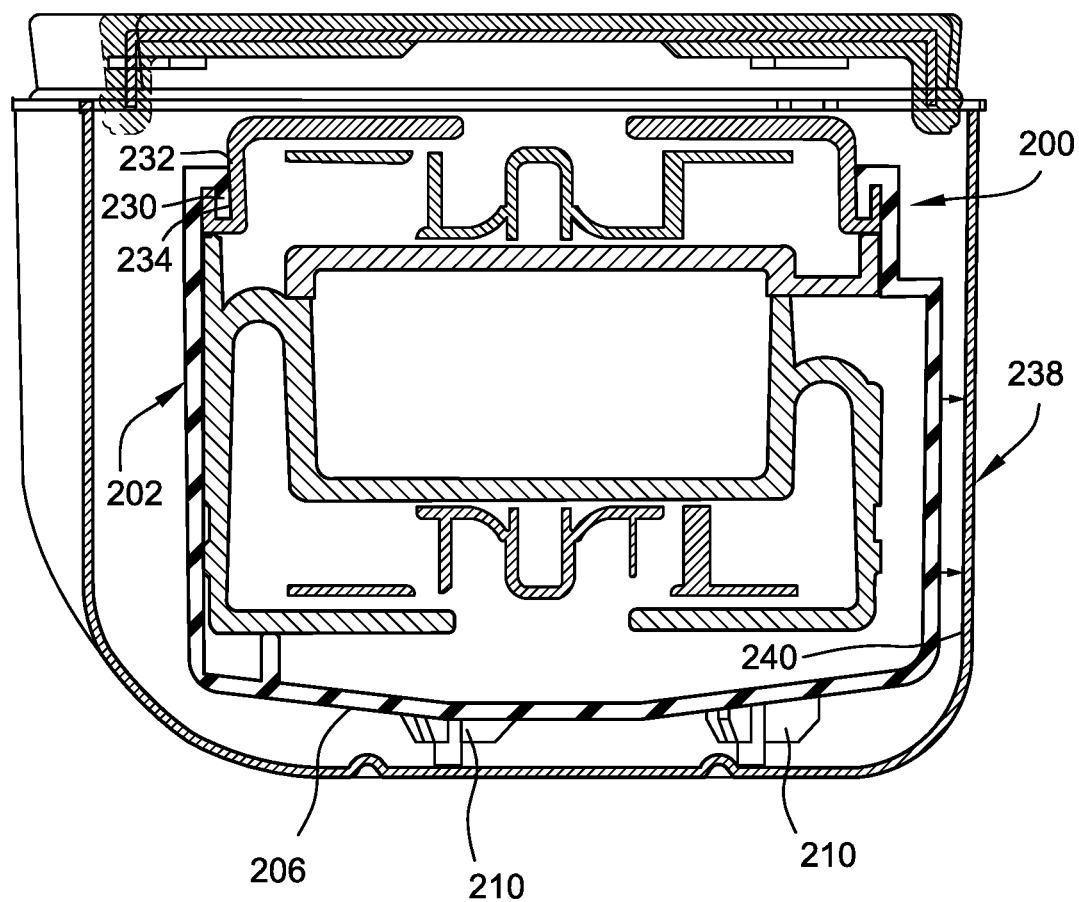
FIG. 21 is a cross-section of a blower motor and sleeve assembly located within a chassis enclosure.

When applied over the motor body as shown in FIGS. 20 and 21, the rim 222 of the sleeve engages the peripheral rim of the top cover 232 in a snug, elastic fashion, with lip 230 seated in a circular groove 234 in the cover. This elastic engagement provides a sufficient seal to prevent escape of air/gas from the space between the motor body and the sleeve.

FIG. 21 illustrates the blower motor assembly located within a chassis enclosure 238. It will be appreciated that when pressurized gas/air flows between the stage 1 and stage 2 volutes radially between the blower motor assembly 200 and the flexible sleeve 202), the flexible sleeve may be expanded radially outwardly into at least partial engagement with an interior wall 240 of the chassis enclosure 238. In this condition, vibrations will still be isolated by the air cushion inside the sleeve. In other words, the pressurized inter-stage gas/air thereby at least partially supports the blower motor assembly in a manner that isolates vibration while it also cushions the motor from damage during rough handling, transport, etc. In this regard, the resilient and flexible support feet 210 replace the springs 28, thus eliminating discrete components that can be difficult to handle and assemble.

A hole 236 in the shoulder 224 (FIG. 17) is utilized for wires connected to the blower motor within the motor body. Alternatively, a notch could be provided in the upper lip or rim 222, opposite the aperture 218.

The flexible sleeve 202 may be made of any suitable flexible material, such as rubber, silicone, silicone rubber or a thermoplastic elastomer (TPE).

Incorporation of a flexible sleeve permits the size of the blower motor assembly to be reduced since the interstage air/gas now performs two functions in one space, i.e., the flowpath between stages and a vibration isolating and bump cushioning element. In addition, the device may be made quieter since more space is made available to the inlet muffler volume. A further advantage is the elimination of the flexible seal portion 76 of the top cover as described hereinabove.

g) Alternative Blower Motor Assembly Embodiment

Figure 23:
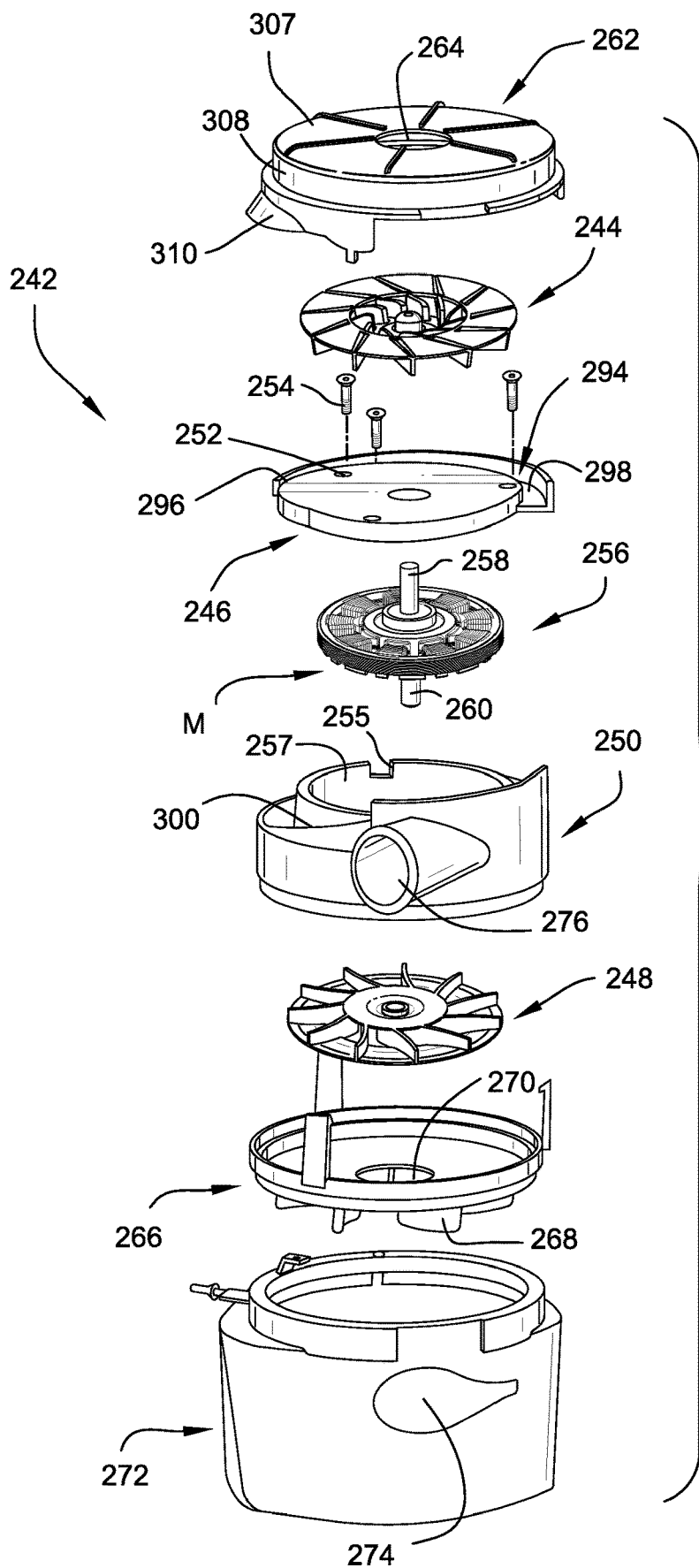
FIG. 23 is an exploded assembly view of a blower motor assembly in accordance with another embodiment.

FIG. 23 is an exploded view of another alternative embodiment of a blower motor assembly 242 including a first stage impeller 244 associated with a first volute component (also referred to herein as a motor cap or end bell) 246 and a second stage impeller 248 associated with a second volute component (also referred to as the motor body) 250. The blower motor assembly is axially stackable so capable of automatic assembly. Additionally, the volute components are axially compact, and sandwiched between upper and lower lids as described below.

The first and second volute components 246, 250 are coupled together with the motor M therebetween. For example, the first volute component 246 may include a plurality of holes 252 to receive threaded screws 254 for fastening the first volute component to the second volute component provided with aligned threaded holes for receiving the screws 254. Alternatively, or in addition, the second volute component 250 can be adhesively coupled to the first volute component 246, or the first volute component can be press fit onto the second volute component.

A rotor 256 of the motor is positioned within between volute components 246 and 250, and the rotor includes a first shaft end 258 coupled to the first impeller 244 and a second axially aligned shaft end 260 coupled to the second stage impeller 258. A top lid or cover 262 includes an inlet 264 and is positioned over the first impeller, and a bottom lid or cover 266 is positioned under and adjacent the second stage impeller 248. The bottom lid includes a plurality of vanes 268 surrounding an inlet 270. Thus, the top lid or cover 262 in cooperation with the first volute component 246 define a chamber or first volute 247 (FIG. 24) in which the first impeller 244 is located, while the lower lid or cover 266 in cooperation with the underside of the second volute component 250 defines, in combination with the lower lid or cover 266 another chamber or second volute 251, directly below a bottom wall 253 of the second volute component 250, in which the second impeller 244 is located. An inter-stage gas path between the first and second volutes is described in greater detail below.

A flexible motor sleeve 272 (FIGS. 23, 24, 35 and 36) surrounds substantially the entire assembly, but includes a cut out portion 274 to receive the outlet 276 of the second volute component 250. The sleeve 272 is an elastomeric component that dampens vibration and/or resonance of internal components. The use of the sleeve 272 may result in fewer parts as compared to common motor assemblies. The sleeve 272 may be insert-molded onto aluminium, or it may co-molded onto the top and/or bottom lids.

Figure 24:
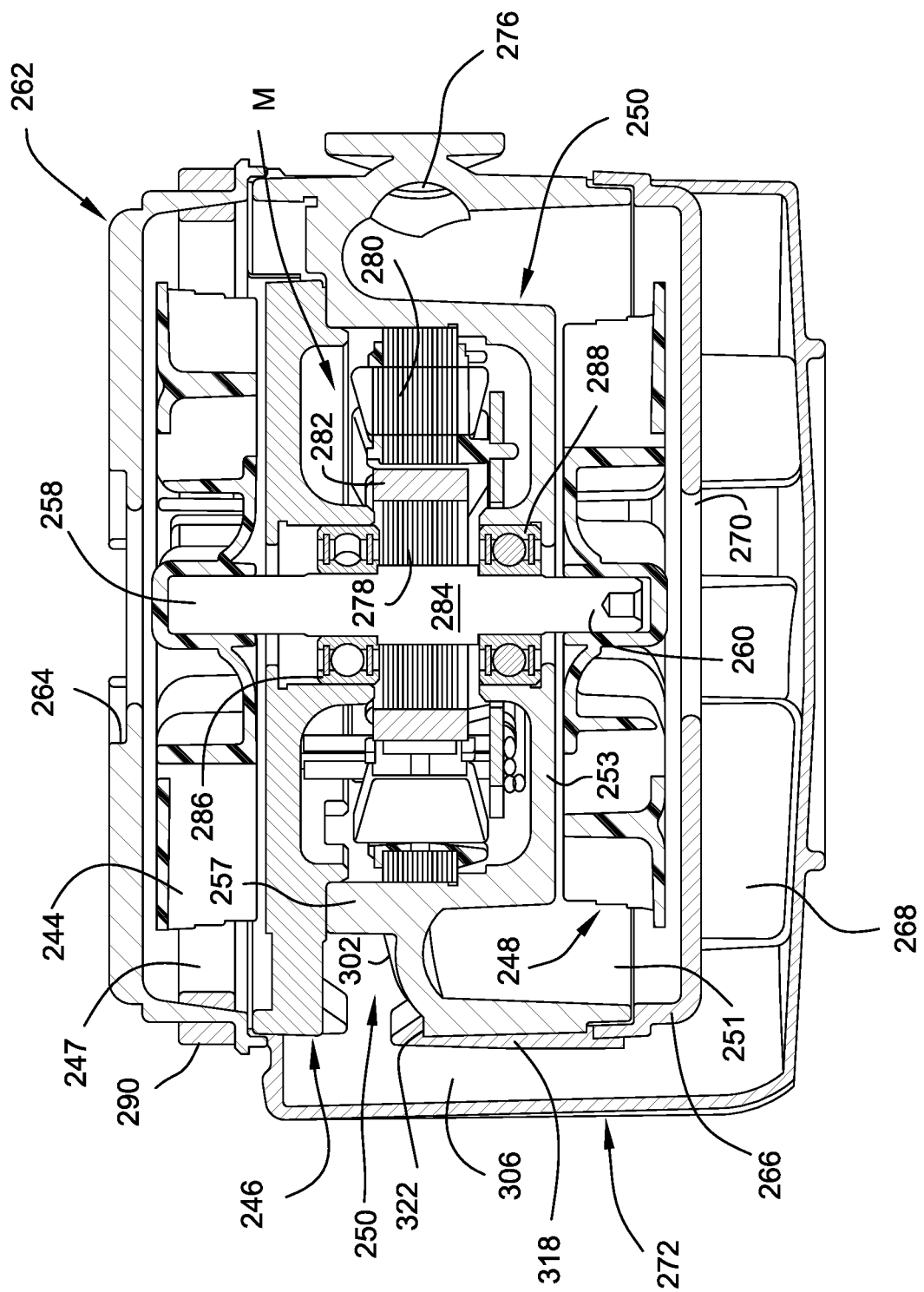
FIG. 24 is a section view of the assembled blower motor assembly of FIG. 23.
Figure 33:
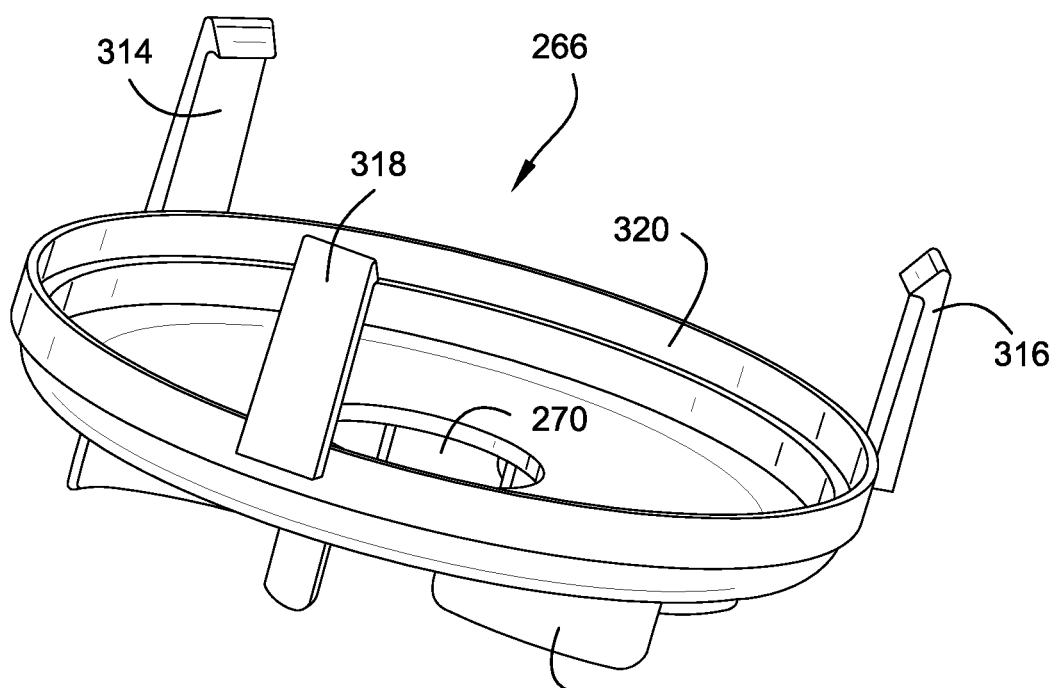
FIG. 33 is a perspective view of the bottom lid or cover taken from FIG. 23.
Figure 34:
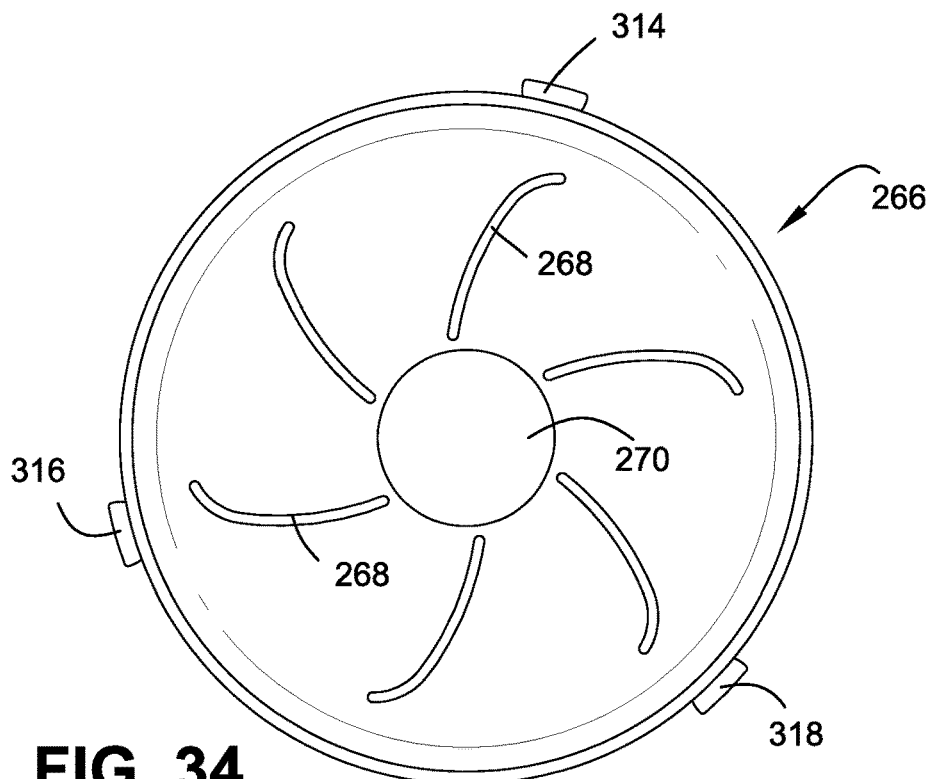
FIG. 34 is a bottom plan view of the bottom lid or cover shown in FIG. 33.
Figure 35:
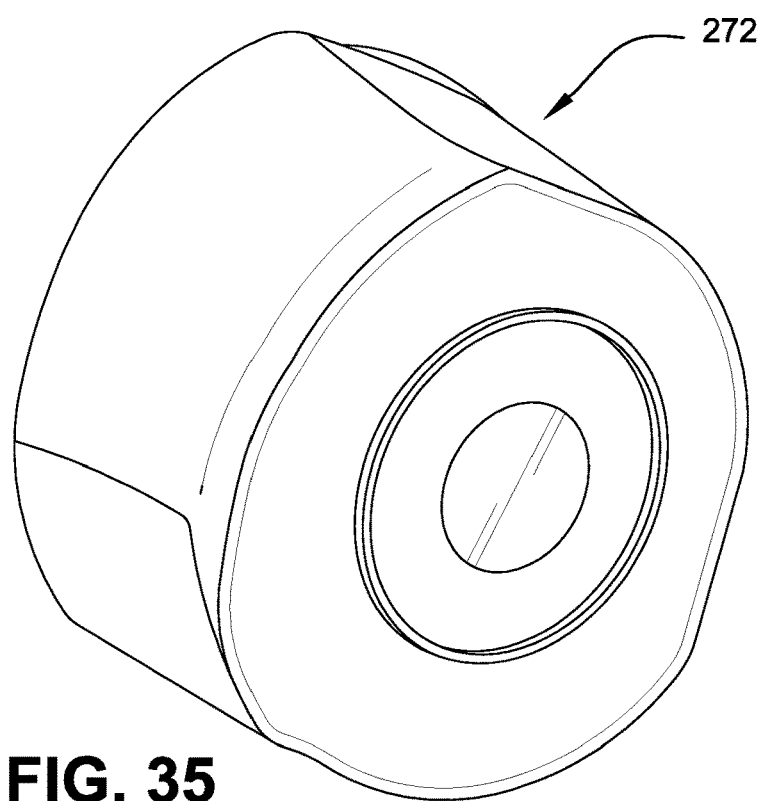
FIG. 35 is a perspective view of a flexible sleeve taken from FIG. 23.
Figure 36:
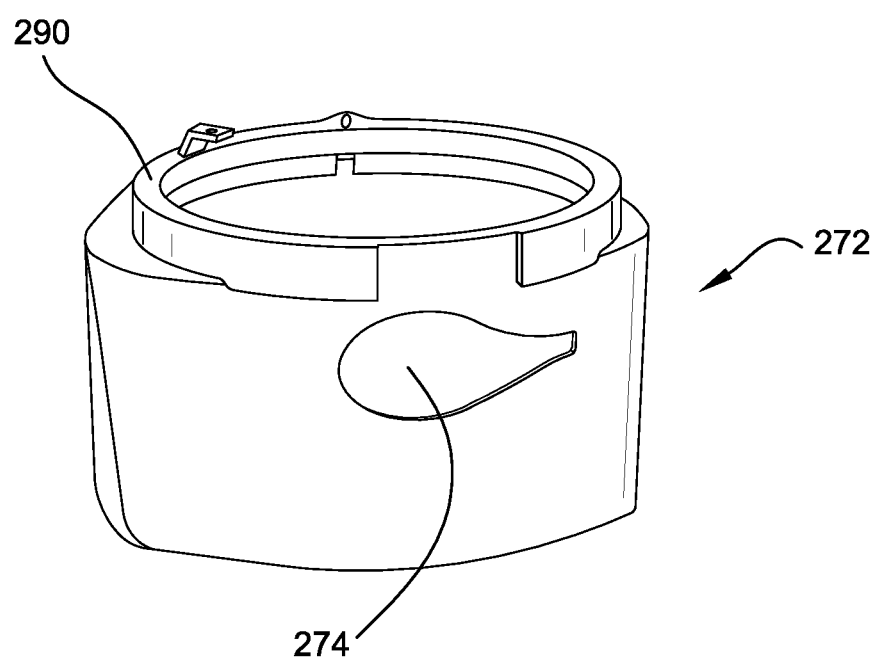
FIG. 36 is a another perspective view of the sleeve shown in FIG. 23.

FIG. 24 shows additional details of the motor M and its positional relationship to the first and second volutes. The motor M includes a laminated stack 278, a plurality of windings 280 and rotor magnet 282. The motor shaft 284 (which includes shaft ends 258, 260) is supported by upper and lower bearings 286, 288. Further, the volute components 246, 250 are at least partially nested, which provides for a compact and space saving design, particularly in the axial direction, while the sleeve 272 also helps conserve space in a radial direction. The sleeve 272 is sealingly coupled to the motor assembly, e.g., using a thickened portion 290 of silicone around its upper surface, as shown in FIGS. 24 and 33, stretched about the edge of the upper lid or cover 262.

Figure 25:
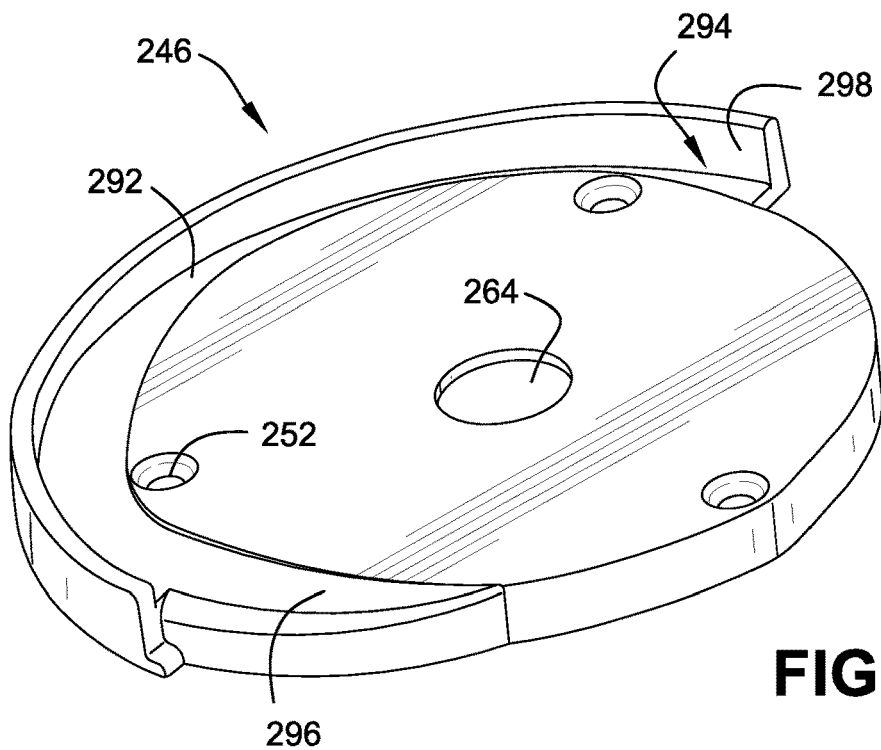
FIG. 25 is a perspective view of a first volute component used in the embodiment illustrated in FIGS. 23 and 24.
Figure 26:
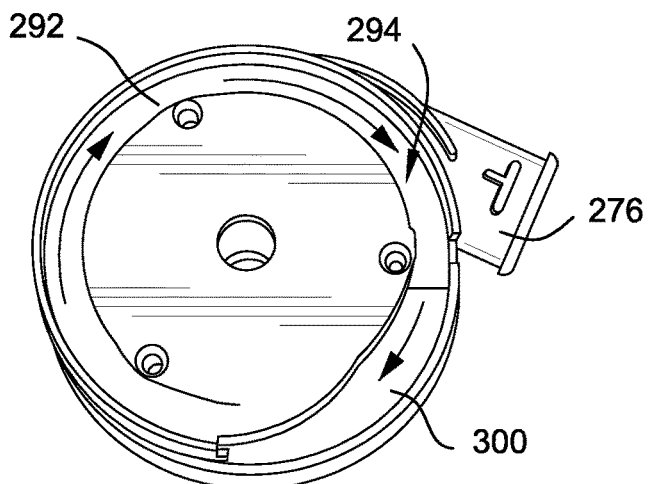
FIG. 26 is a perspective view of assembled first and second volute components from the embodiment illustrated in FIGS. 23 and 24.
Figure 27:
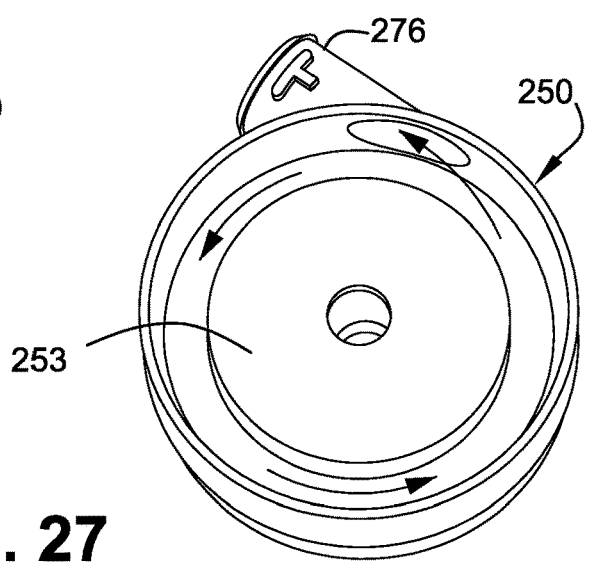
FIG. 27 is a perspective view of the assembly of FIG. 26 but in an inverted position.

FIG. 25 shows the first volute component 246 with a part annular ramp surface 292 defining a flow channel 294 extending approximately 180° with increasing depth from an "inlet" end of the channel at 296 to an "outlet" end 298. FIGS. 26-30 illustrate the first and second volute components 246, 250 in combination, without the motor. These figures illustrate the inter-stage path of a gas (for example, air) as it is channeled from the first impeller 244 to the second impeller 248, and hence from the first volute 247 to the second volute 251. This inter-stage path is generally concentric relative to the motor shaft 284 and defines a transition zone designed to ramp downwardly in a spiral fashion from the first volute to the second volute. More specifically, the first two arrows in FIG. 26 lie on surface 292 of channel 294 in the first volute, and the third arrow lies on a more steeply-inclined ramp surface on the outside of the second volute component 250, which, in turn, continues along a substantially horizontal surface 302, also on the second volute component 250.

Figure 28:
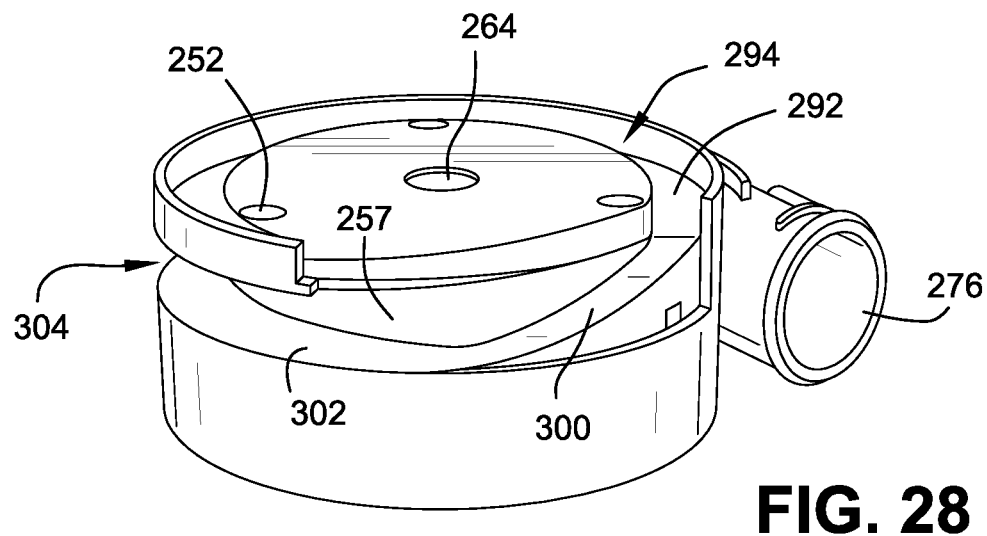
FIG. 28 is another perspective view of the assembled first and second volute components shown in FIGS. 26 and 27.
Figure 29:
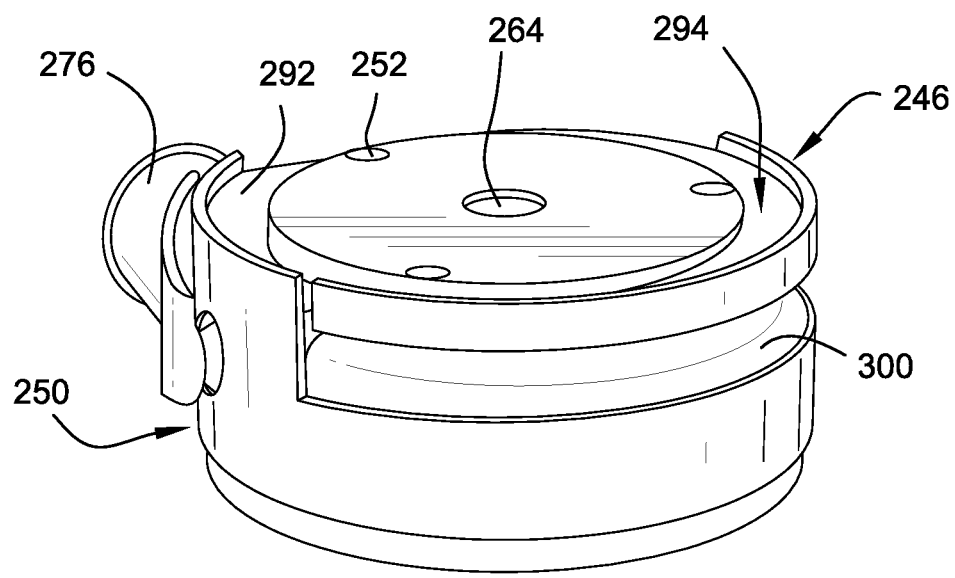
FIG. 29 is a perspective view similar to that shown in FIG. 28 but rotated approximately 180°.
Figure 30:
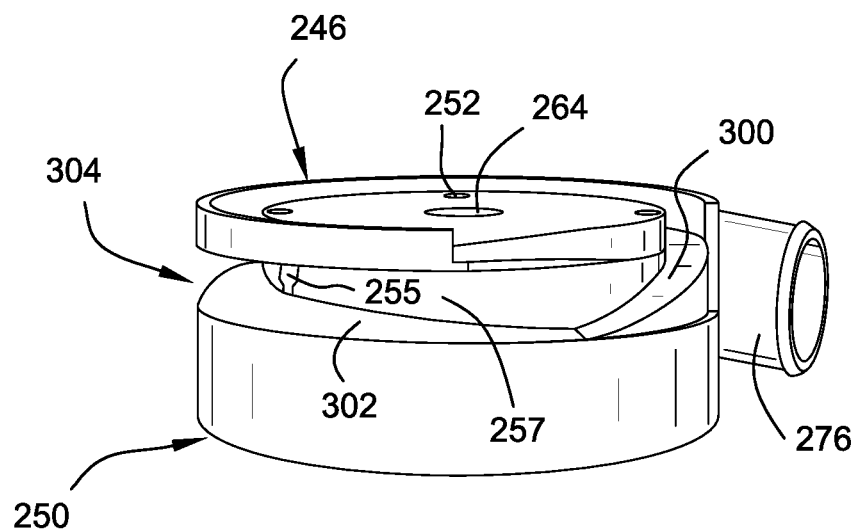
FIG. 30 is a perspective view similar to FIG. 28 but with the assembled components rotated slightly in a counter-clockwise direction and tilted to a more upright position.

This arrangement allows the gas to decelerate as it ramps down and expands. Note that a groove 304 is now formed between surface 302 and the underside of the first volute component 246. This groove is tapered in the circumferential direction, with surface 302 rising slightly toward the first volute component 246 as best seen in FIGS. 28-30 so as to encourage forward and continued movement gas remaining in the first volute 246 and any decelerated gas in the inter-stage path, about the second volute component 250. A notch 255 in an inner wall 257 of the second volute component 250 permits passage of the motor wires (not shown).

In use, the gas spirals downwardly through the transitional zone and enters into the area 306 which also extends below the bottom lid or cover 266 and then into the opening 270 and into the second volute 251. Vanes 268 reduce the degree of swirl or spin as the gas flows to the second volute where the gas is then swirled about the volute 251 via second impeller 248 and upwardly to the outlet 276.

Figure 31:
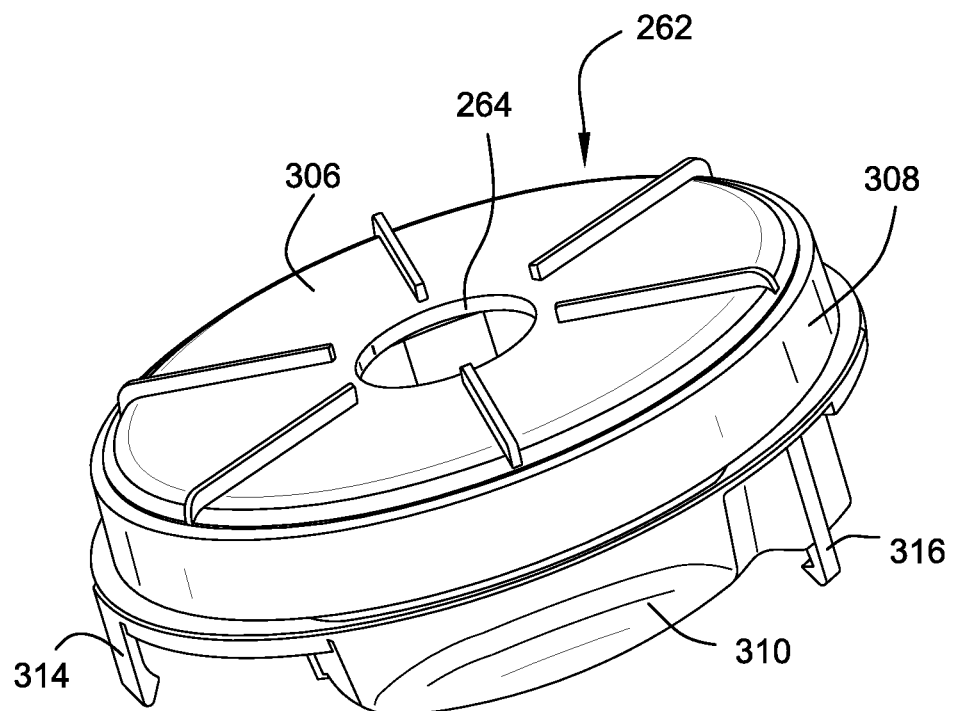
FIG. 31 is a perspective view of the top lid or cover taken from FIG. 23.
Figure 32:
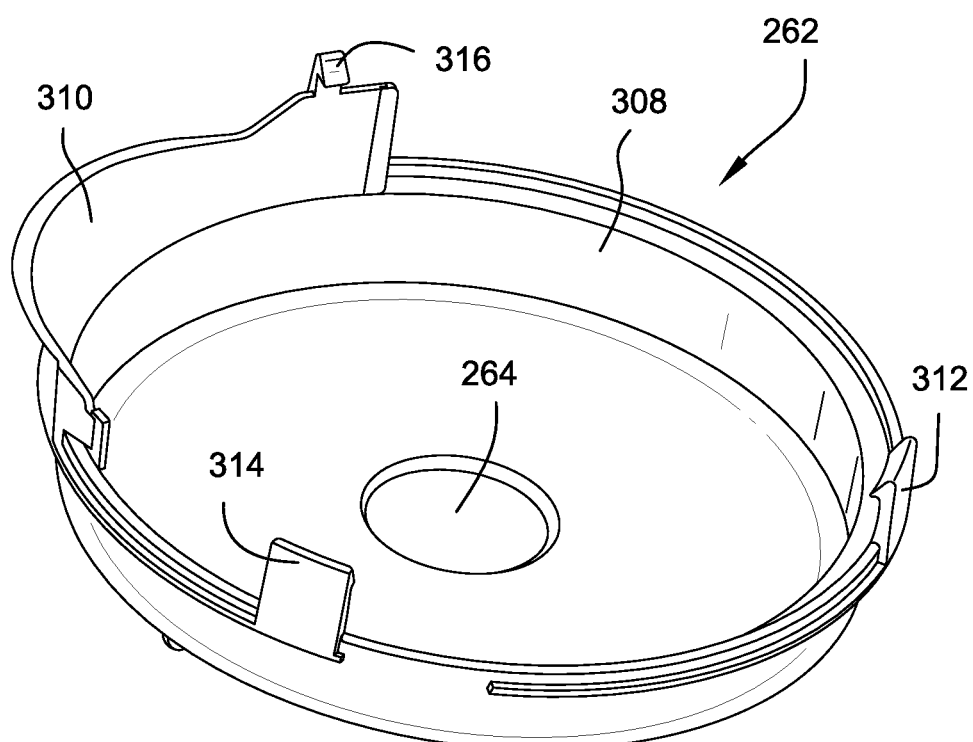
FIG. 32 is a perspective view of the top lid or cover of FIG. 31, but with the lid or cover in an inverted position.

As shown in FIGS. 23 and 31 the top lid or cover 262 includes a flat upper surface 307 provided with the inlet opening 264 and a peripheral depending skirt 308. An outlet hood 310 depends from a portion of the skirt 308 and covers the transition zone between the first and second volutes, allowing the gas to move radially outwards to fill the stage-to-stage or inter-stage path. Attachment tabs 312, 314 and 316 serve to attach the upper lid to the underside of the first volute component 246.

With reference to FIGS. 23, 24, 33 and 34, the bottom lid 266 is also formed with upstanding attachment tabs 314, 316, 318 on skirt 320 adapted to engage a peripheral rim 322 on the second volute component 250. With the first volute component 246 securely fastened to the second volute component 250 via screw fasteners 254, and with the upper and lower lids 262, 266 snap-fit onto, or otherwise attached to the first and second volutes components, respectively, it will be appreciated that assembly of the compact unit is easily achieved. The flexible sleeve 272, best seen in FIGS. 23 and 24, 35 and 36 is telescopically received over the motor/volute assembly so as to further define the inter-stage gas path, as described above in connection with the embodiment illustrated in FIG. 21, and the manner in which the sleeved blower motor assembly described in connection with FIGS. 23-36 operates is otherwise similar to the embodiment shown in FIGS. 16-21.

With regard to the impellers 244 and 248, each of the blades may be tapered towards the outside of the impeller, e.g., to axially move the blade tips from the cut-off to decrease the blade pass tone. This structure may also maintain the cross-sectional area as moving out from the center of the impeller closer to constant. This will encourage the airflow to maintain contact with the blades, to increase efficiency and/or decrease noise. In another variant, the surfaces of the components adjacent the impellers could be tapered to match the impeller shapes, thereby providing a constant distance between those surfaces and the impeller blade edges. The impellers 244, 248 also have an alternating shroud design as described above which can also help reduce noise.

The motor assembly thus described has a low inertia which may allow for use in other applications, e.g., to respond quickly for other therapies and/or to increase response of transducer(s). Further, the temperature of the motor is cooler, and drag from the bearing heat is less due to running the slower speeds of the motor, which helps with reliability. Also, the integrated volutes can help conduct heat into the air path to warm the air, which also has the effect of improving the reliability of the motor. Further, the generated heat can warm the air path, which can be advantageous in cooler conditions. Another benefit is that there is less pressure across the bearings as a result of multistage air path.

h) Additional Features

In another variant, a mode of operation may be provided where the flow through the motor is intentionally oscillated to be faster than the breathing rate. The results can be useful for diagnostic purposes, e.g., to determine open or closed airway or for other diagnostic purposes. Suitable oscillation techniques are described in commonly owned U.S. Pat. No. 5,704,345. Such information can also be used to activate an active vent.

A thermal cutout may be provided on the motor. The cutout would monitor the heat in the motor casing, and shut off power in the event of an overheat.

In another embodiment, the impellers could be structured to spin in either the same directions or in opposite directions.

In yet another variant, the blower assembly could include a port for water egress, such as holes at the bottom of the sleeve, to protect against water pooling at the bottom of the motor if it spills back from an attached humidifier.

Further, the motor housing body and the first and second volute components may be integrated.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention. For example, while many aspects of the invention relate to double ended or multi-stage blowers (two or more stages), single stage blowers are also contemplated. On the other hand, each end of the motor shaft may include multiple impellers. Also, the various embodiments described above may be implemented in conjunction with other embodiments, e.g., aspects of one embodiment may be combined with aspects of another embodiment to realize yet other embodiments. Further, each component or feature alone for any given embodiment may constitute an independent embodiment. In addition, while the invention has particular application to patients who suffer from OSA, it is to be appreciated that patients who suffer from other illnesses (e.g., congestive heart failure, diabetes, morbid obesity, stroke, barriatric surgery, etc.) can derive benefit from the above teachings. Moreover, the above teachings have applicability with patients and non-patients alike in non-medical applications.

What is claimed is:

1. A positive airway pressure (PAP) device for generating a supply of pressurized breathable gas for treatment of sleep disordered breathing, the PAP device comprising:
    a blower to pressurize gas, the blower including a motor having a shaft and an impeller provided to the shaft, the impeller comprising:
    a top shroud having a frusto-conical shape, and the top shroud forming a center opening;
    a bottom shroud having a substantially planar shape; and
    a plurality of vanes extending between the top shroud and the bottom shroud,
    each of the plurality of vanes comprising a leading edge and a trailing edge,
    wherein the leading edge extends radially inwardly beyond the top shroud and is exposed through the center opening, and
    wherein the trailing edge comprises surface disturbances structured and arranged to reduce noise.

2. The PAP device according to claim 1, wherein the surface disturbances comprise a plurality of indentations.

3. The PAP device according to claim 1, wherein the surface disturbances comprise serrations.

4. The PAP device according to claim 1, wherein the surface disturbances comprise steps.

5. The PAP device according to claim 1, wherein the bottom shroud includes a hub or bushing adapted to receive the shaft.

6. The PAP device according to claim 1, wherein each of the plurality of vanes includes a height that tapers along its radial length.

7. The PAP device according to claim 1, wherein the top shroud extends to a radially outer tip of each of the plurality of vanes.

8. The PAP device according to claim 1, wherein the impeller comprises 11 vanes.

9. The PAP device according to claim 1, wherein each of the plurality of vanes includes a cross-sectional thickness that is tapered along at least a portion of its length.

10. The PAP device according to claim 1, wherein each of the plurality of vanes is curved along at least a portion of its length.

11. The PAP device according to claim 1, wherein each flow passage formed between adjacent ones of the plurality of vanes is structured to enlarge towards the trailing edge.

12. The PAP device according to claim 1, wherein an outer diameter of the top shroud is greater than a maximum radial extent of each of the plurality of vanes.

13. The PAP device according to claim 1, wherein the impeller comprises a polycarbonate material and/or polypropylene material.

14. The PAP device according to claim 1, wherein the impeller comprises a molded one piece construction.

15. The PAP device according to claim 1, wherein the shaft has two ends and at least one said impeller provided to each said end.

16. A PAP system for delivery of pressurized breathable gas to a patient for treatment of sleep disordered breathing, the PAP system comprising:
    a PAP device according to claim 1;
    a patient interface adapted to form a seal with a patient's face; and
    air delivery tubing to deliver the supply of pressurized breathable gas from the PAP device to the patient interface.

17. A positive airway pressure (PAP) device for generating a supply of pressurized breathable gas for treatment of sleep disordered breathing, the PAP device comprising:
    a blower to pressurize gas, the blower including a motor having a shaft and an impeller provided to the shaft, the impeller comprising:
    a plurality of vanes, each of the plurality of vanes comprising a leading edge and a trailing edge, wherein the trailing edge comprises surface disturbances structured and arranged to reduce noise; and substantially planar wall portions to connect adjacent ones of the plurality of vanes.

18. The PAP device according to claim 17, wherein the surface disturbances comprise a plurality of indentations.

19. The PAP device according to claim 17, wherein the surface disturbances comprise serrations.

20. The PAP device according to claim 17, wherein the surface disturbances comprise steps.

* * * * *